United States Patent [19]
Kittrell et al.

[11] Patent Number: 5,419,323
[45] Date of Patent: May 30, 1995

[54] METHOD FOR LASER INDUCED FLUORESCENCE OF TISSUE

[75] Inventors: Carter Kittrell, Houston, Tex.; Robert M. Cothren, Cleveland Heights, Ohio; Michael S. Feld, Waban, Mass.; Joseph J. Baraga, Somerville, Mass.; Kyungwon An, Cambridge, Mass.; Rebecca Richards-Kortum, Austin, Tex.; Richard P. Rava, Marlboro, Mass.; Young D. Park, Chicago, Ill.; Anand Mehta, Cambridge, Mass.; Paola Taroni, Como, Italy; Lucene Tong, Boston; Ramachandra R. Dasari, Lexington, both of Mass.

[73] Assignee: Massachusetts Institute of Technology, Cambridge, Mass.

[21] Appl. No.: 720,465

[22] PCT Filed: Nov. 17, 1989

[86] PCT No.: PCT/US89/05174

§ 371 Date: May 7, 1993

§ 102(e) Date: May 7, 1993

[87] PCT Pub. No.: WO90/06718

PCT Pub. Date: Jun. 28, 1990
(Under 37 CFR 1.47)

[51] Int. Cl.[6] ............................................. A61B 6/00
[52] U.S. Cl. ............................................. 128/653.1
[58] Field of Search ............................ 128/633-634, 128/664-666, 653.1; 606/3, 14-16

[56] References Cited

U.S. PATENT DOCUMENTS

| Re. 31,815 | 1/1985 | Alfano | 128/665 |
|---|---|---|---|
| 4,162,405 | 7/1979 | Chance et al. | |
| 4,178,917 | 12/1979 | Shapiro | 128/665 |
| 4,236,526 | 12/1980 | Richard | 128/633 |
| 4,556,057 | 12/1985 | Hiruma et al. | |
| 4,641,650 | 2/1987 | Mok | |
| 4,718,417 | 1/1988 | Kittrell et al. | |
| 4,737,628 | 4/1988 | Lovoi | |
| 5,106,387 | 4/1992 | Kittrell et al. | 606/15 |

FOREIGN PATENT DOCUMENTS

| 3210593A | 2/1982 | France. |
|---|---|---|
| 2203831A | 10/1988 | United Kingdom. |
| 929050 | 4/1978 | U.S.S.R. . |
| 88/09145 | 12/1988 | WIPO. |
| 89/02718 | 4/1989 | WIPO. |
| 90/05563 | 5/1990 | WIPO. |

OTHER PUBLICATIONS

Goth et al., "Multifiber Optically-Shielded Catheter For Laser Angiosurgery" *Optical Fibers in Medicine II* 713:58-63 (1986).

Cothren et al. "Controlled Light Delivery For Laser Angiosurgery" *J. Quantum Elec.* QE-22 (Jan. 1986).

Kittrell et al. "Diagnosis of Fibrous Arterial Atherosclerosis Using Fluorscence" *Applied Optics* 24(15):2280-2281 (Aug. 1 1985).

Hoyt et al., "Remote Biomedical Spectroscopic Imaging of Human Artery Wall" *Lasers in Surgery and Medicine* 8:1-9 (1988).

(List continued on next page.)

Primary Examiner—Angela D. Sykes
Attorney, Agent, or Firm—Hamilton, Brook, Smith & Reynolds

[57] ABSTRACT

A method for laser induced fluorescence of tissue in which laser radiation is used to illuminate and induce fluorescence in the tissue under study to determine the chemical composition or pathologic condition of tissue. The laser radiation and the retrieved fluorescing radiation can be conveyed through a catheter using an array of optical fiber. The fluorescence spectrum of the tissue can be displayed and analyzed to obtain information regarding the chemical composition and medical condition of the tissue inside the human body.

17 Claims, 19 Drawing Sheets

OTHER PUBLICATIONS

Satori et al., "Autofluorescence Maps of Atherosclerotic Human Arteries–A New Techniques in Medical Imaging" *J. Quantum Elec.* QE–23 (10:1794–1797 (Oct. 1987).

Montan et al. "Multicolor Imaging and Contrast Enhancement in Cancer–tumor Localization Using Laser–induced Fluorescence in Hematoporphyrin–derivative–bearing Tissue" *Optics Letters* 10(2):56–58 (Feb. 1985).

Andersson et al., "Tumour Localization By Means of Laser–Inducted Fluorescence in Hematoporphyrin Derivative (HPD)–Bearing Tissue" *Proc. Seventh Int'l Conf. Hawaii* :401–406 (Jun. 24–28, 1985).

Alfano et al., "Laser Induced Fluorescence Spectroscopy From Native Cancerous and Normal Tissue" *J. Quantum Elec.* QE–20(12):1507–1511 (Dec. 1984).

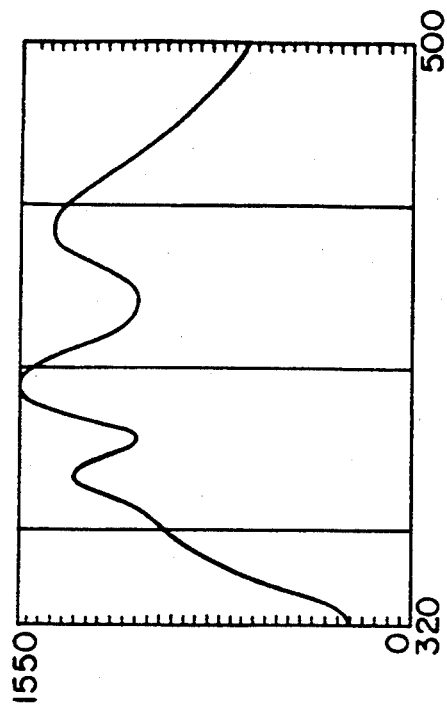
Fig. 1a Normal intima
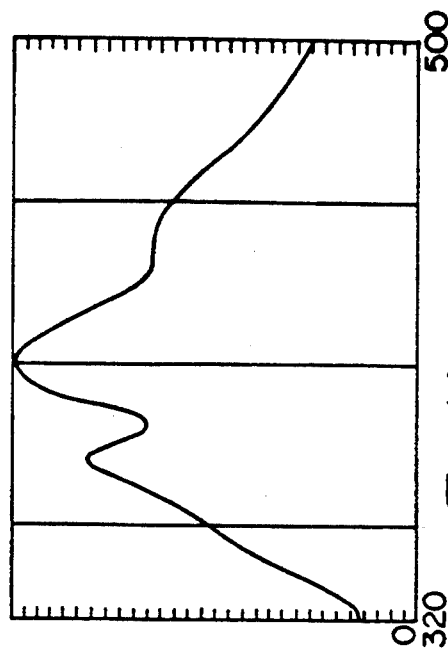
Fig. 1b Fiberous plaque
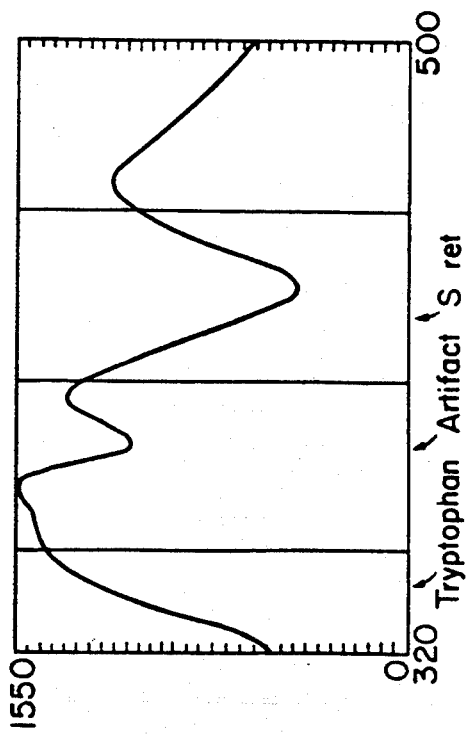
Fig. 1c Fatty plaque
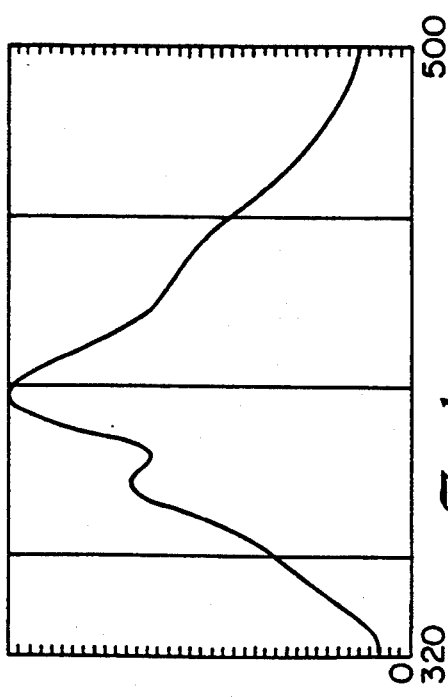
Fig. 1d Calcified plaque

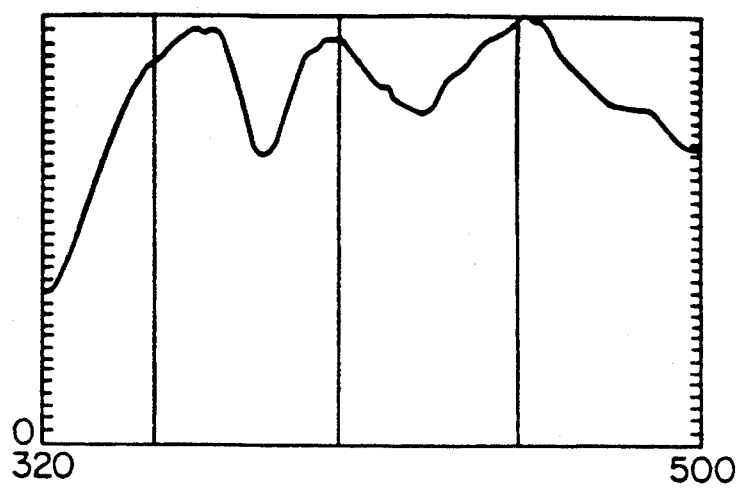
*Fig. 2a* Normal: ablated into, but not through, normal media
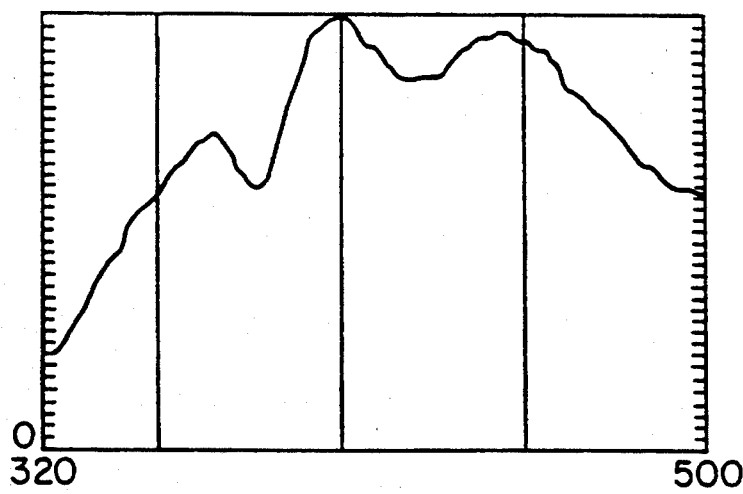
*Fig. 2b* Plaque: ablated into, but not through, normal media

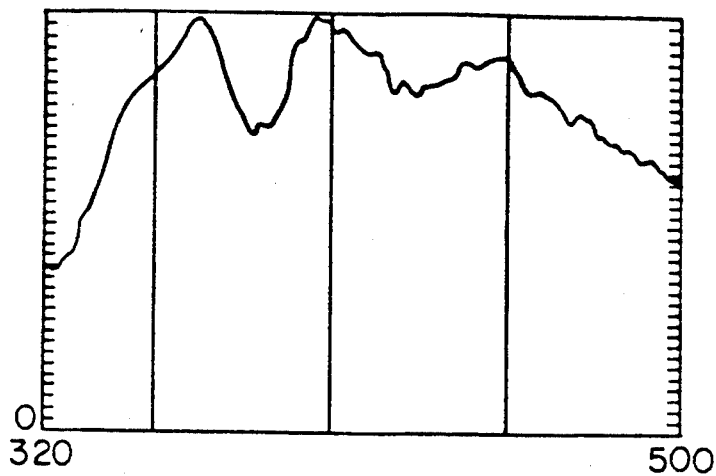
Fig. 2c  Plaque/normal: ablated through plaque into media
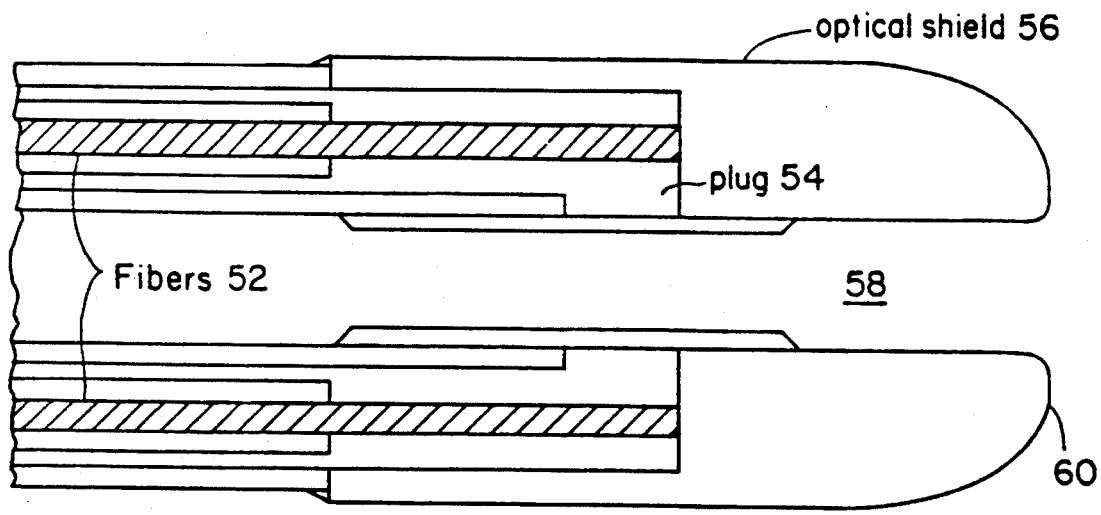
Fig. 3C
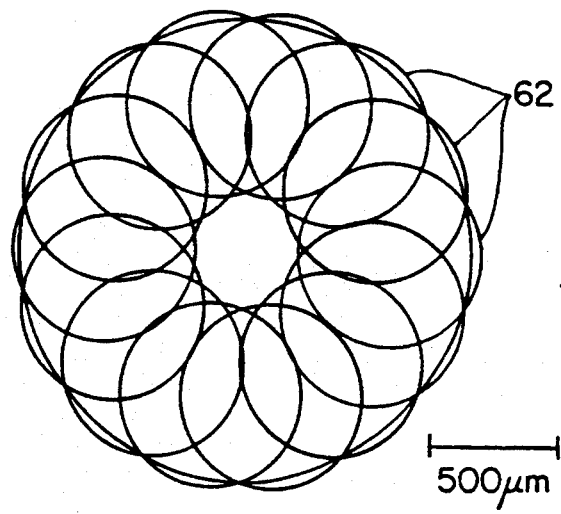
Fig. 3D LIF spectra of bulk normal aorta, excited at 306, 308, and 310nm. (a.u.=arbitrary units)

LIF spectra excited at 306, 308, and 310nm.
B) Atherosclerotic plaque  C) Atheromatous plaque

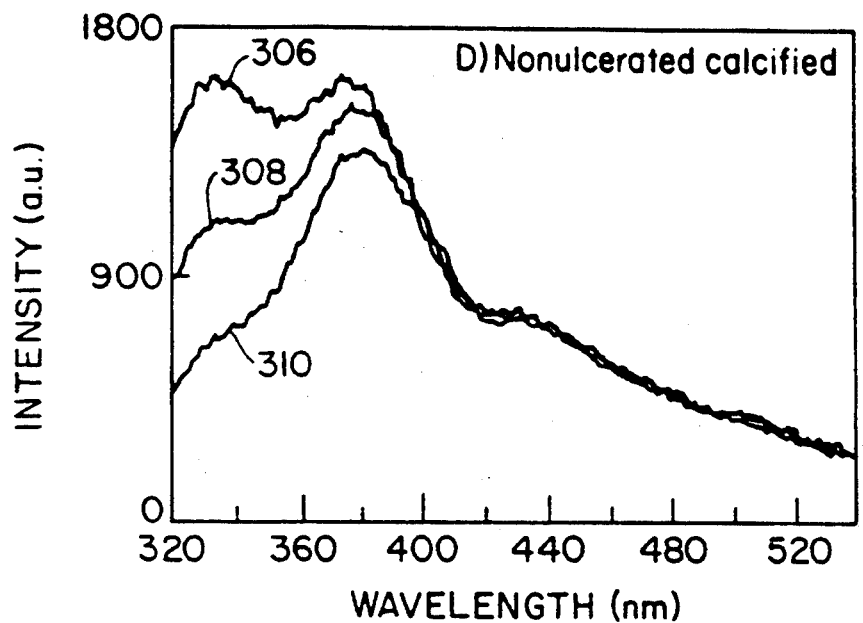
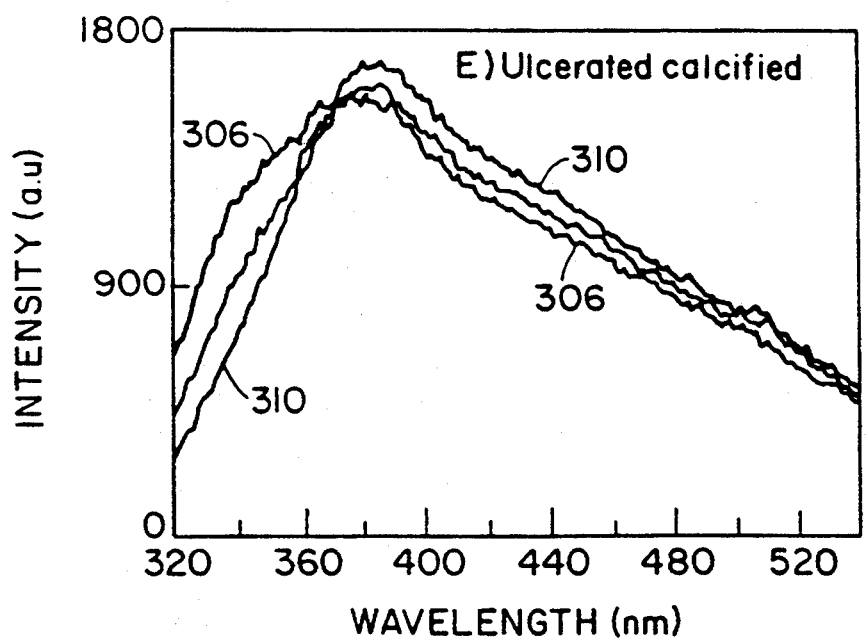
LIF spectra excited at 306, 308, and 310nm.
D) Nonulcerated calcified plaque.
E) Ulcerated calcified plaque.

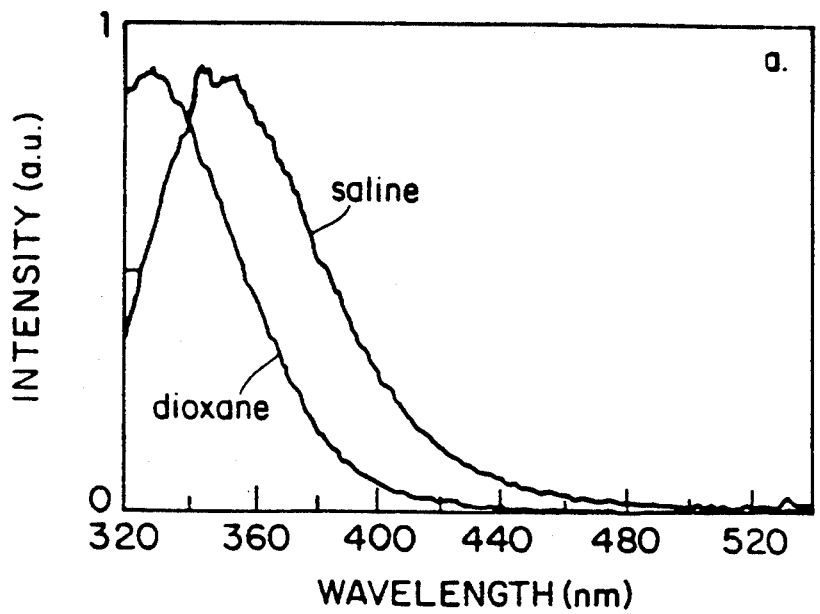
A) LIF emission spectra of L-tryptophan (Sigma) in dioxane (400μM; $\lambda_x$=285nm) and saline solution (40μM; pH=7.4; $\lambda_x$=308nm)
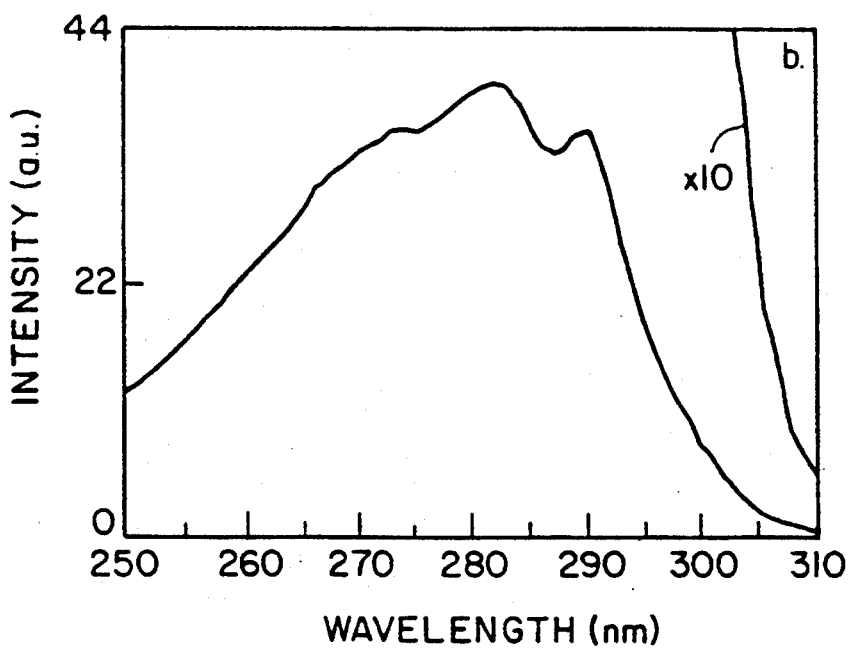
B) Excitation scan of tryptophan in dioxane ($\lambda_m$=330nm; normalized at $\lambda_x$=308nm) [recorded on spectrofluorimeter].

LIF emission spectra, $\lambda_x = 308$nm
A) Collagen Type I, hydrated (Calbiochem, Bovine Achilles Tendon).
B) Elastin, hydrated (Sigma, Bovine Neck Ligament).

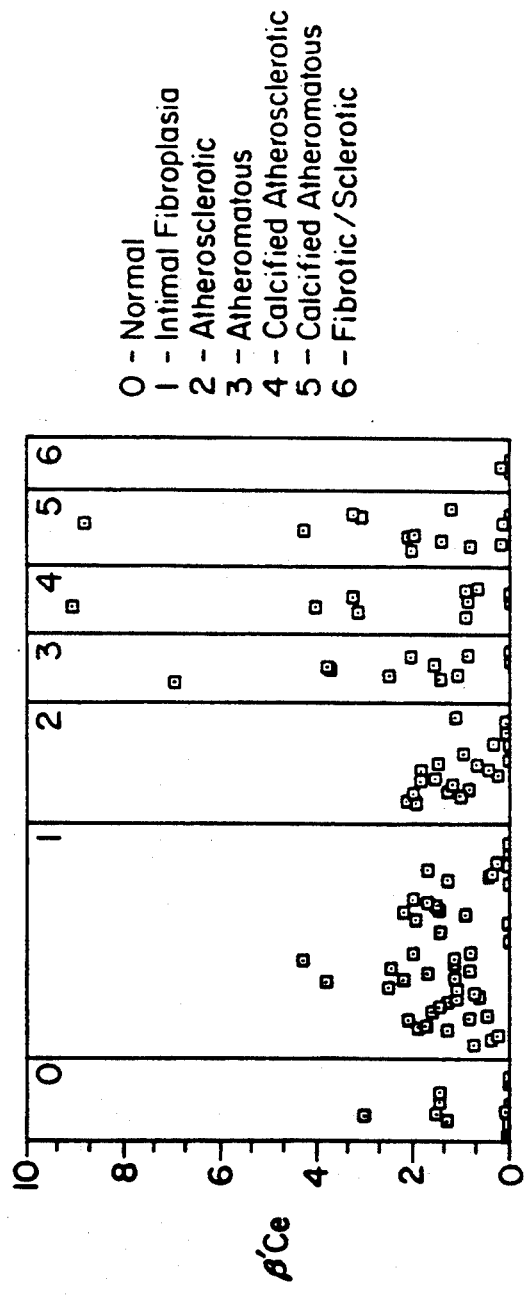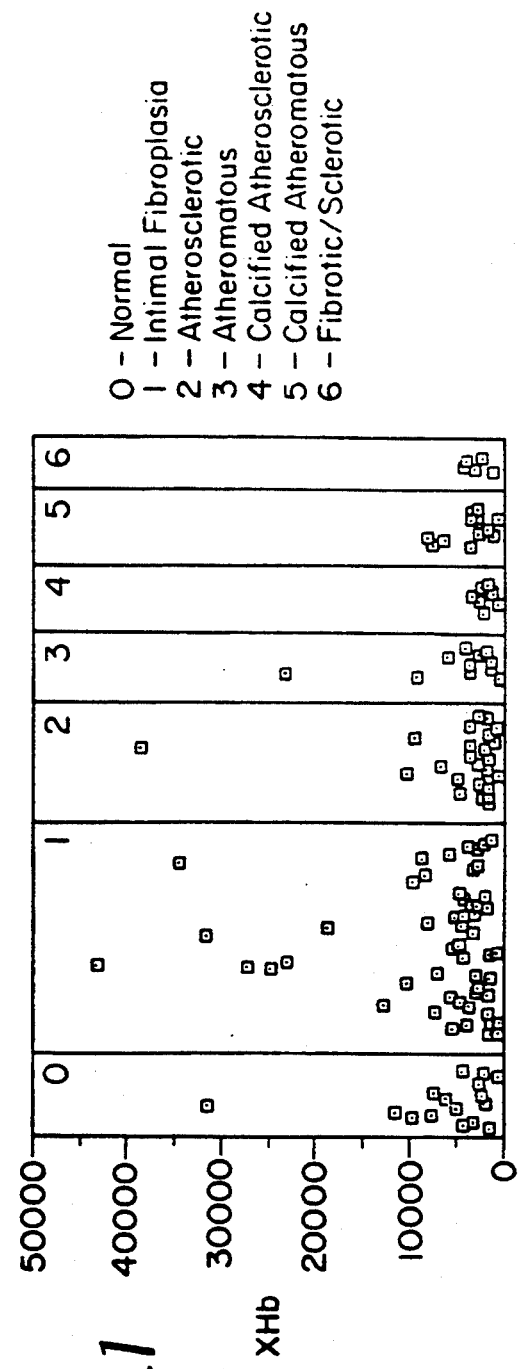

METHOD FOR LASER INDUCED FLUORESCENCE OF TISSUE

BACKGROUND OF THE INVENTION

The present invention relates to optical and laser spectroscopy and, in particular, laser induced fluorescence (LIF) spectroscopy which has recently been explored as a technique for medical diagnosis.

It is known that fluorescence spectroscopy can be used to diagnose the presence of atherosclerosis in human artery wall, emphasizing the use of empirically defined algorithms to determine tissue type from fluorescence spectra. For example, using 476 nm LIF spectroscopy, Kittrell et al., "Diagnosis of Fibrous Atherosclerosis Using Fluorescence", *Applied Optics,* 24, 2280 (1985), have demonstrated that such an empirical algorithm can be used to differentiate normal aorta and early atherosclerotic plaque in vitro. Fluorescence spectra of normal aorta and fibrous plaque were differentiated by the peak to valley ratio of the fluorescence intensity at 600 nm to the intensity at 580 nm.

Catheters employing optical fibers for the illumination, viewing and treatment of tissue are now used with sources of laser radiation for a variety of medical applications. Through the insertion of the catheter into a human artery or bodily cavity, laser radiation of a given wavelength can be used to illuminate tissue within the body such that the tissue fluoresces. Radiation generated by tissue fluorescence is then conveyed by one or more of the optical fibers to the proximal end of the catheter where it can be analyzed to yield information about the tissue under examination.

SUMMARY OF THE INVENTION

The method of the present invention relates to the diagnosis of tissue and particularly targeting of chromophores in soft tissue with optical radiation and analyzing returning radiation to determine the type and abundance of those chromophores. By utilizing the laser induced fluorescence of chromophores contained in the tissue the concentration of those chromophores yields significant diagnostic information about the tissue. The method provides a technique for rapid identification and diagnosis of tissue without the highly invasive procedures currently in use.

Chromophores that naturally occur in tissue respond to incident light by several processes. Absorption of light by the tissue will occur based on the characteristics of each of the chromophores that are present. Single or multiple wavelength excitation will provide a characteristic spectrum or profile of the tissue being illuminated. Some of the chromophores in the tissue will fluoresce depending upon the excitation wavelength or wavelengths so that the fluorescence emission will define a characteristic profile for that tissue.

Note that the emission also has a fluorescence lifetime which may be measured and analyzed to reveal important diagnostic information. In addition, the chemical moieties in the tissue exhibit inelastic or Raman scattering, which also provide useful spectral information.

The total spectrum is the sum of the individual contributions of the many chemical constituents of the tissue. When additional excitation wavelengths are used, chromophore excitation is also altered, some emitting at stronger intensities and some weaker. The overall profile changes as each individual contribution changes. The use of many excitation wavelengths assists in the identification of the chromophores present in the tissue.

In particular, tuning through the absorption edge of a chromophore at a particular wavelength can result in sharp changes in the emission spectrum. Tuning close to the edge allows the spectral profile to be adjusted like a dimmer switch relative to the other chromophore contributions to the spectrum.

Since different types of tissue have different chemical composition, spectroscopy can be used to identify different chromophores present in the tissue being diagnosed. By measuring the presence and amount of the chromophores, the tissue type can be more fully characterized. For increased accuracy in diagnosis, or to help distinguish between similar but non-identical tissues, several wavelengths can be used to target several chromophores.

Excitation of naturally occurring chromophores with ultraviolet light in the 305–310 nm range generates fluorescence spectra (330–500 nm) which are useful in characterizing tissue type and condition. Various types of arterial tissue, including normal, diseased aorta and coronary artery have been examined to obtain spectra in bulk tissue using collection optics.

In vivo applications utilize a catheter containing one or more optical fibers which is inserted into an artery, bodily cavity or tissue surface such that the distal end is positioned adjacent to the tissue to be diagnosed. A specific chromophore or group of chromophores is then selected for analysis by selecting an irradiating wavelength known to excite the targeted chromophore or group of chromophores. A source of optical or laser radiation is then coupled to the proximal end of selected fibers within the catheter and the tissue being analyzed is then illuminated with radiation, causing it to fluoresce. The scattered tissue and fluorescence light from the tissue is then transmitted along the fibers to the proximal end of the catheter, where it is analyzed to determine the chromophores and, hence, diagnose the tissue.

The laser wavelength can be tuned to match the peak absorption of the chromophore being detected. Alternatively the wavelength or wavelengths can be selected to discriminate between adjacent peaks of known chromophores. It can also be tuned to the absorption edge of a particular chromophore to identify its contribution to the spectrum. Other characteristics of the tissue can be ascertained by exciting two chromophores and determining the ratio of the fluorescence peaks.

This present method provides information regarding the chemical constituents of the tissue being examined. In particular, the presence of certain fluorophores can be detected whose presence is an indicator of specific tissue pathology. Tissue fluorescence spectra can be deconvolved to yield more information regarding the fluorescence spectra. The method shows that in an optically thick sample of tissue the observed fluorescence signal is not simply the sum of the fluorescent contributions from individual chromophores but that frequency dependent absorption must be taken into account to properly deconvolve the spectrum.

A further embodiment of the present invention relates to a method of tissue analysis involving the use of time-decay laser induced fluorescence spectroscopy. The monitoring of fluorescence decay times also provides information regarding the chromophores present in human tissue.

Human aortic tissue and coronary artery tissue has been excited in the range of 305-312 nm to produce fluorescence decay signals in the range of 320 nm to 500 nm. This has provided information regarding the presence of certain fluorophores in the tissue, including the contribution thereof to the spectral lineshape.

Note that these procedures are performed on endogeneous tissue, that is, tissue that has not been treated with dyes or stains commonly used to enhance the fluorescence characteristics of biological materials or tissue. The present method thus provides for the rapid diagnosis of "native" or endogeneous tissue, including tissue within human subjects accessed by catheters having optical fibers to couple precisely controlled amounts of radiation to the tissue.

The above, and other features of the invention including various novel details of construction and combination of parts, will now be more particularly described with reference to the accompanying drawings and pointed out in the claims. It will be understood that the particular method of laser induced fluorescence of tissue embodying the invention is shown by way of illustration only and not as a limitation of the invention. The principal features of this invention may be employed in various embodiments without departing from the scope of the invention. For example, the present method can be used in diagnosing the condition of various kinds of tissue.

BRIEF DESCRIPTION OF THE DRAWINGS

FIGS. 1A, 1B, 1C and 1D are graphical illustrations of emission spectra resulting from a 310 nm excitation wavelength of normal intima (1A), fibrous plaque (1B), fatty plaque (1C) and calcified plaque (1D) where the typical pulse energy is 150 nJ.

FIGS. 2A, 2B and 2C are graphical illustrations of emission spectra of ablation damaged tissue excited at a 305 nm wavelength. FIG. 2A shows the emission spectrum of normal tissue after ablation into but not through the tissue. FIG. 2B shows the emission spectrum after ablation into, but not through fatty plaque. FIG. 2C shows the emission spectrum of tissue after ablation through plaque into normal tissue.

FIGS. 3A, 3B, 3C and 3D illustrate a probe devices and the optical system used in performing the method of the present invention.

FIGS. 7A-7E are graphical illustrations of the fluorescence emission intensity plotted versus wavelength for the these different excitation wavelengths 306 nm, 308 nm, and 310 nm for A) bulk normal aorta, B) atherosclerotic plaque, C) atheromatous plaque, D) nonulcerated calcified plaque, and E) ulcerated calcified plaque.

FIGS. 8A and 8B are schematic graphical illustrations plotting intensity (arbitrary units) versus wavelength of an emission scan (8A) with excitation at 308 nm, and an excitation scan (8B) of L-tryptophan in tris buffer with the emission peak at 350 nm.

FIG. 20 is a scatter plot of $\beta'_{Ce}$ for the measured samples.

FIG. 21 is a scatter plot of $\chi_{Hb}$ for the measured samples.

DETAILED DESCRIPTION

Excitation of naturally occurring chromophores with ultraviolet light in the 305-310 nm range generates fluorescence spectra (330-500 nm) which are useful in characterizing tissue type and condition. Various types of arterial tissue, including normal and diseased aorta and coronary artery, have been examined to obtain spectra in bulk tissue using collection optics described in more detail below.

The excitation source for Laser Induced Fluorescence (LIF) in a preferred embodiment of the invention was a dye laser pumped by a 10 Hertz Nd:YAG laser and frequency doubled. Gated integration minimized background noise by taking advantage of the ten nsec duration pulse. The results demonstrate that the tissue LIF has several spectral features which vary with tissue type and condition.

The spectra taken in bulk tissue indicate that normal aorta can be distinguished from plaque, and that different types of plaque (fibrous, fatty and calcified) also exhibit different emission spectra (FIG. 1). The tissue tolerance to the low power diagnostic ultraviolet light is good. Even after substantial exposure, distinctive spectral features remain even though there is a significant loss of fluorescence energy. After ablation with a high power argon-ion laser, the remaining aortic plaque can be distinguished from damaged normal media (FIG. 2). The excitation wavelength is changed from 310 nm to 305 nm in this particular example. When plaque has been ablated away exposing the underlying media, the ultraviolet LIF spectrum more closely matches that of normal media which had no overlying plaque, that is, this technique determines when the plaque layer has been penetrated.

Spectral features are very sensitive to excitation wavelength; changing from 305 nm to 310 nm makes a substantial difference in the emission lineshape. Tryptophan fluoresces strongly with 285 nm excitation and dominates the spectra, but the long wavelength weak absorption "tail" occurs in the 305–310 nm range, so that a careful selection of the excitation wavelength will act as a chromophore "dimmer switch" and control the size of the tryptophan emission peak at about 340 nm.

Figure 7A:
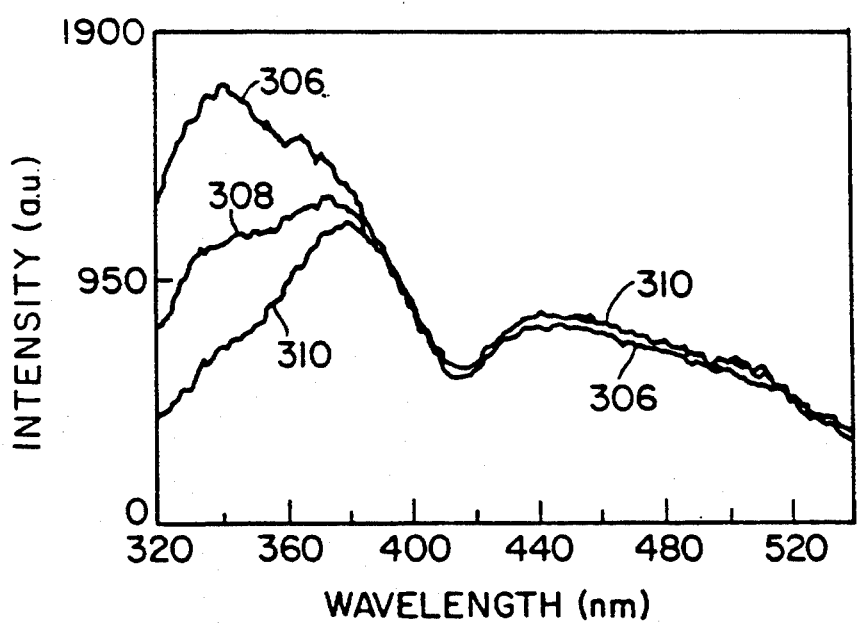
Figure 7B:
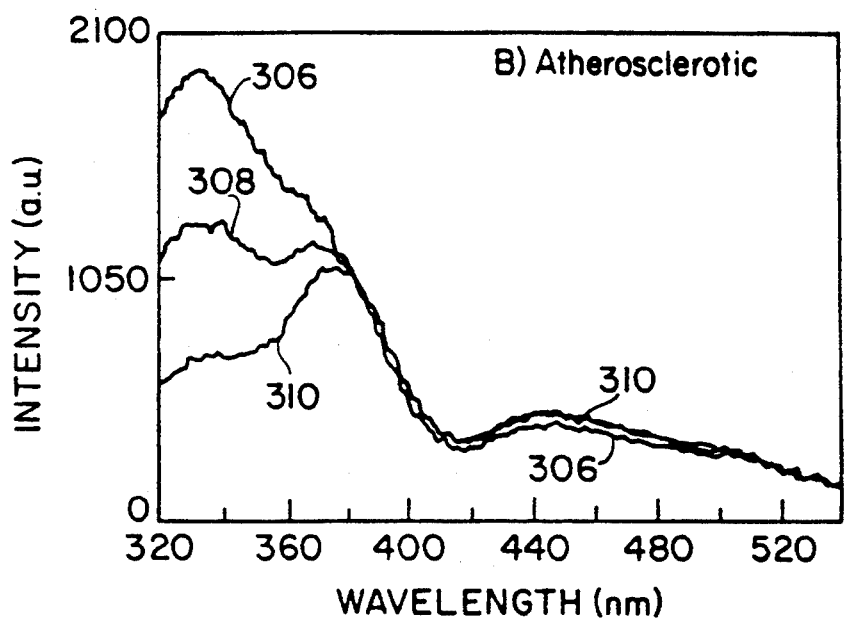
Figure 7C:
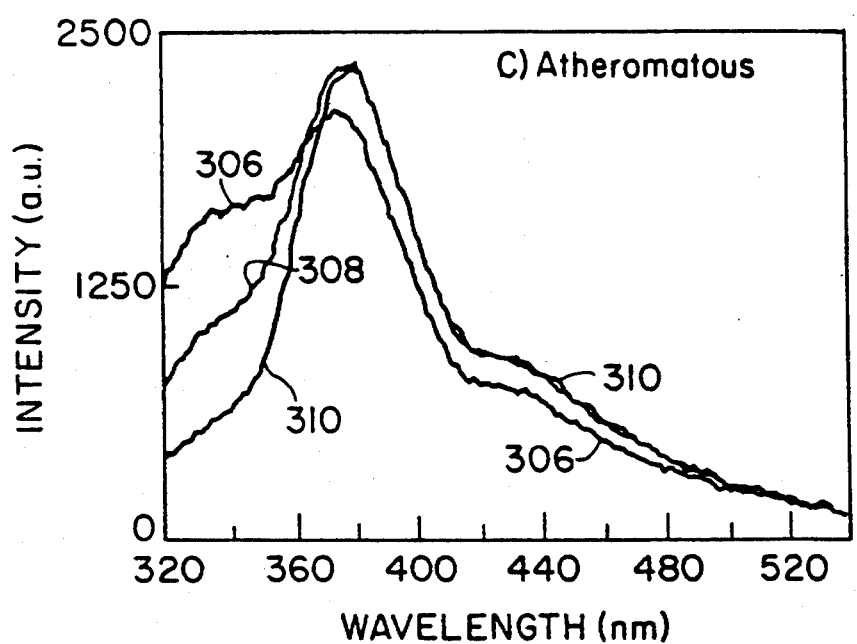

FIG. 7A displays three emission spectra, excited at 306, 308 and 310 nm, from a typical sample of normal aorta. The emission lineshape is extremely sensitive to the excitation wavelength, as a very small change in wavelength results in a quite different spectrum. These spectra illustrate the sharpness of the transition between the short wavelength and long wavelength bands. At 306 nm excitation, the large emission peak at 340 nm dominates the spectrum. A minor shoulder at 380 nm and a valley at 418 nm are also present. With a change in excitation of merely 4 nm to 310 nm, the 340 nm peak disappears, leaving a peak at 380 nm, which was apparently hidden under the larger 340 nm emission band at 306 nm excitation. The lineshape at wavelengths longer than 380 nm remains relatively unchanged. The emission scan at 308 nm has a lineshape intermediate to the 306 nm and 310 nm spectra, and can be regarded as the transitional point at which the short and long wavelength bands contribute in roughly equal amounts to the total emission.

In order to derive physically meaningful information from this fluorescence, it is necessary to identify the tissue components and the individual molecular groups responsible for the observed emission lineshapes. In a multicomponent dilute solution or an optically thin section of tissue, the fluorescence signal is a simple sum of the fluorescence contributions of the individual components. In an optically thick material such as bulk tissue, however, the effects of fluorescence reabsorption can produce profound alterations in the emission line-shapes of these components. These effects must be understood and separated from the intrinsic fluorescence of the components in order to accurately identify the active species.

FIGS. 7B–7E display LIF spectra excited at 306, 308, and 310 nm of typical samples of an atherosclerotic plaque, an atheromatous plaque, a nonulcerated calcified plaque, and an ulcerated calcified plaque. Similar to normal aorta, the fluorescence lineshapes of each can be divided into a short and a long wavelength band. The short wavelength band is assigned to tryptophan, and the long wavelength band to collagen/elastin using equivalent arguments as those employed for normal aorta. The differences in lineshapes between the atherosclerotic lesions and normal are suggested below to be a result of a change in the relative concentrations of these components. Additional, distinct fluorophores in the atherosclerotic specimens are not observed at these excitation wavelengths.

The LIF lineshapes of each type of atherosclerotic lesion are quite distinct, and certain spectral features of each are worth noting. The intensity of the short wavelength band relative to the long band is slightly higher in the atherosclerotic plaque (FIG. 7B) than in normal aorta (FIG. 7A). Among the atherosclerotic lesions, this intensity ratio is largest in the atherosclerotic plaque, smaller in the atheromatous and nonulcerated calcified plaques, and smallest in the ulcerated calcified plaque. However, all the samples show a similar excitation behavior for this band, as the fractional change in fluorescence emission intensity at 340 nm when changing from 310 nm to 306 nm scans, in which the interference from the tryptophan band is minimal. The hemoglobin valley at 418 nm is present in varying degrees, being most prominent in the atherosclerotic plaque specimen, less so in the atheromatous and nonulcerated calcified plaques, and apparently absent in the ulcerated calcified plaque. In the atheromatous and nonulcerated calcified plaque specimens, the long wavelength fluorescence tail (440–540 nm) is markedly reduced, indicating an increase in the collagen contribution to this band relative to that of elastin. The atherosclerotic plaque spectrum also shows a reduced 440–540 nm fluorescence tail compared with normal, although this reduction is not as great as in the case of atheromatous and nonulcerated calcified plaques. The 440–540 nm tail in the spectra of the calcified plaque, on the other hand, shows no such reduction as compared with normal.

The fluorescence peak at 340 nm is attributed to the aromatic amino acid tryptophan, a known UV fluorophore. Tryptophan in aqueous solution shows a 60 nm FWHM fluorescence band peaking at 348 nm when excited in the ultraviolet. The peak position is somewhat sensitive to environment; for instance, tryptophan powder peaks at 330 nm when excited with 308 nm. Tryptophan emission (FIG. 8A) peaks between 330 and 350 nm, depending on its local environment. In the buffered saline, it peaks at 350 nm, while in 1,4 dioxane (a hydrophobic solvent), it peaks at 329 nm. The short wavelength band in optically thin normal aorta spectra peaks around 332 nm, so it appears than tryptophan is located in a more hydrophobic environment in the tissue. For example, tryptophan emission from the common intracellular protein actin in aqueous solution (pH7) has a high fluorescence quantum yield (0.24) and a peak emission wavelength of 332 nm. The assignment of the short wavelength band to tryptophan has been confirmed by more extensive fluorescence excitation-emission matrix studies of human aorta. The excitation spectrum of tryptophan is shown in FIG. 8B.

The appearance of a peak in an emission spectrum is thus associated with a distinct fluorophore having its maximum emission at that wavelength. The 450 nm peak in the present spectra is the result of the singly-peaked broadband fluorescence at 387 nm, distinct from the fluorescence at 340 nm, modulated by reabsorption near 417 nm. It has been demonstrated that the valleys in their visible LIF spectra of arterial wall above 500 nm are due to reabsorption by oxy-hemoglobin or other porphyrin type absorbers. The Soret absorption band of oxy-hemoglobin occurs at 415 nm, matching the wavelength of the valley in our spectra. This was confirmed by the absence of this valley in LIF spectra of 4 $\mu$m tissue sections taken with a Leitz UV-fluorescence microscope. Such sections are essentially free of reabsorption; consequently, the absence of the 417 nm valley in the thin section indicates that the valley in our bulk tissue spectra is due to reabsorption of LIF. Similar valleys previously observed in the visible in artery and in breast tissue are due to the same effect.

Figure 9A:
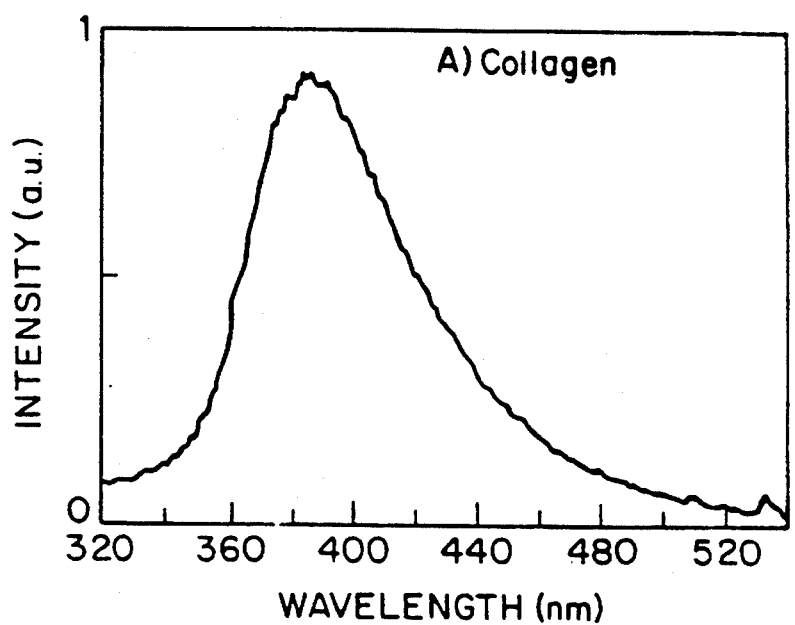
FIGS. 9A and 9B are graphical illustrations of emission spectra at 308 nm excitation for A) collagen with a peak at 383 nm and B) elastin powder with a peak at 379 nm.
Figure 9B:
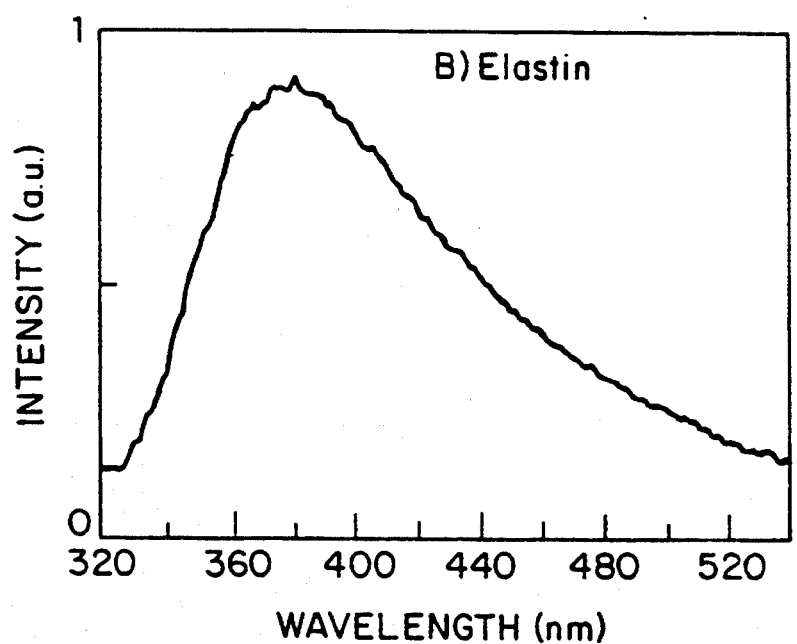

The long wavelength band, peaking at 380 nm, is a combination of collagen and elastin, each of which makes up 20–30% of the dry weight of normal intima. The emission lineshapes of collagen and elastin are similar, with the peak of collagen at 383 nm and that of elastin at 379 nm (See FIG. 9). In addition, both are relatively insensitive to excitation wavelength. However, their emission lineshapes do have an important difference: the collagen bandshape is significantly narrower than the elastin bandshape. For example, the fluorescence intensity of elastin at 480 nm as compared to its peak is 0.3, while that of collagen is 0.1. This distinction allows collagen and elastin to be spectroscopically separated. It is known that several distinct fluorophores may be active in both collagen and elastin. The cross-linking-moieties pyridinoline in collagen and pyridinoline and/or tritryosine in elastin are the fluorophores active at these excitation wavelengths.

Figure 5:
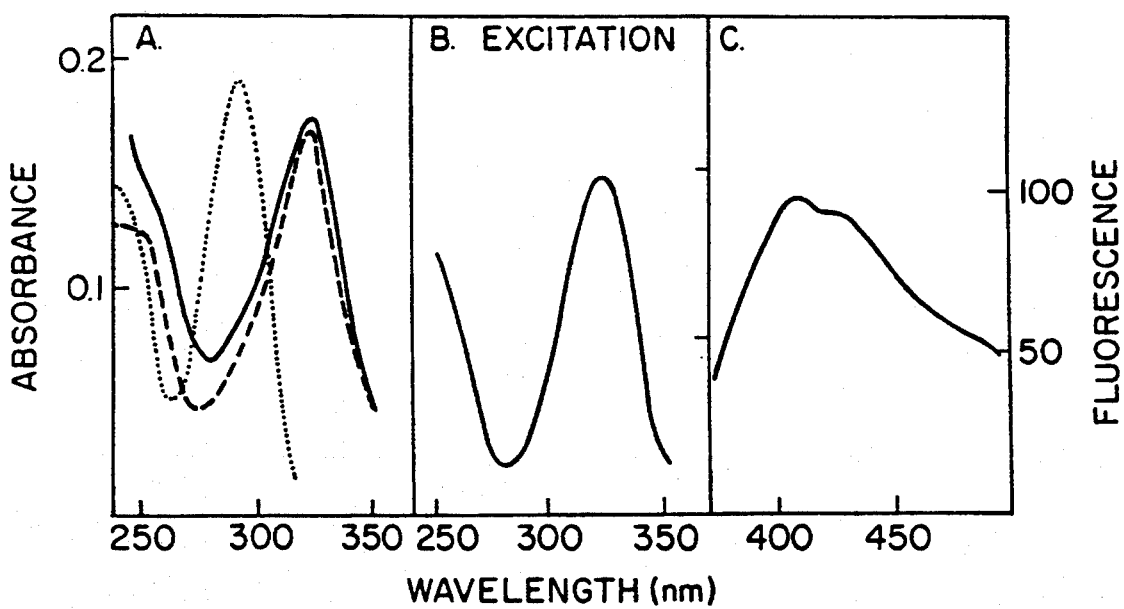
FIG. 5 is a graphical illustration of spectra showing the UV absorption of pyridinoline in 0.1N HCl ( -.-.- ), in 0.1M potassium phosphate buffer, pH 7.4 ( ----- ), and 0.1N NaOH ( ----- ) (FIG. 5A); the activation spectrum in 0.02M potassium phosphate buffer, pH 7.4 with fluorescence at 400 nm (FIG. 5B); and the fluorescence spectrum in 0.02M potassium phosphate buffer, pH 7.4, with activation at 325 nm (FIG. 5C).

In the above example, the excitation wavelength is on the short wavelength absorption maximum of the collagen peak, so the collagen intensity can vary in the opposite direction of tryptophan, and more slowly. Therefore, excitation wavelength can be carefully selected so that tryptophan emission is relatively strong in tissue which contains it, such as normal media; and is relatively weak in tissue with low tryptophan content, such as fatty or calcified plaque. Likewise, pyridinoline is a fluorescent compound found in elastin and collagen (See the absorption spectra of pyridmoline in FIG. 5A) and contributes to the 400 nm signal which is strongest for tissue containing elastin. Thus, correlating observed LIF spectra to tissue composition is used when excitation wavelengths can be selected to enhance differences based on known differences in chemical make-up of different types of tissue.

The argon ion laser tissue ablation substantially reduces the tryptophan contribution, and it appears that heating degrades this chromophore. This is observed as a substantial decrease in fluorescence yield with 280 nm excitation. To compensate for this, the excitation wavelength is shifted to 305 nm for studying ablation-damaged tissue (See FIG. 2). The emission signal from the small amount of tryptophan remaining is enhanced, by using a shorter wavelength, and ablation-damaged plaque and media can be distinguished.

This sensitivity to excitation wavelength should also be considered when studying tissues with a high nucleic acid content. The absorption of nucleic acid overlaps that of tryptophan, but the quantum yield is much less. However, at the tryptophan edge in a region of the trytophan emission spectrum where the intensity varies rapidly as a function of excitation wavelength, there is the potential for relative enhancement of nucleic acid absorption. The emission contributes to the 360 nm range of the LIF tissue spectra. Narrowband excitation is very important; when searching for that wavelength, any strong shorter wavelengths will elicit a powerful response from tryptophan. As explained above, the large valley at 420 nm in the spectra of FIGS. 7A–7E is due to the absorption by hemoglobin in the tissue. This hemoglobin absorption is due to the Soret absorption band of porphyrin. This will not be caused by hemoglobin alone, as the Soret band is characteristic of porphyrins in general.

Figure 6:
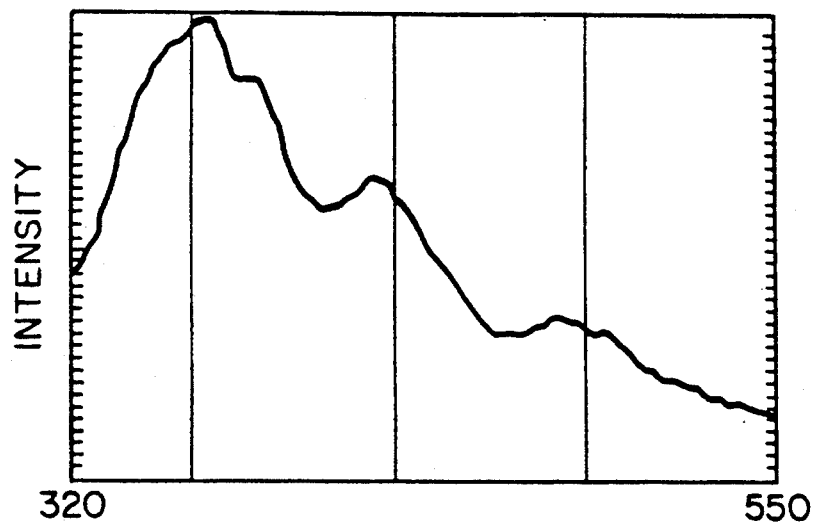
FIG. 6 is a graphical illustration of the emission spectrum of normal aortic tissue taken with a fiber-optic device with excitation at 305 nm.

Spectra (FIG. 6) were recorded using a fiber-optic device (See the more detailed description of the collection system below). An epoxy plug containing a 200 micron core silica fiber was inserted into a 3 mm silica test tube. A central fiber illuminated the tissue and the nine collector ring fibers had the proximal ends placed at the monochromator slit. One collection fiber can be separately connected to a photodiode to monitor laser pulse energy impinging on the tissue, which can be ratioed, or if coupling optics are used, the scattered laser light can be split off near the monochromator. Laser catheter devices used in connection with the present invention have been more fully described in copending U.S. Ser. No. 07/058,675 having a priority date of Mar. 22, 1985.

Figure 3A:
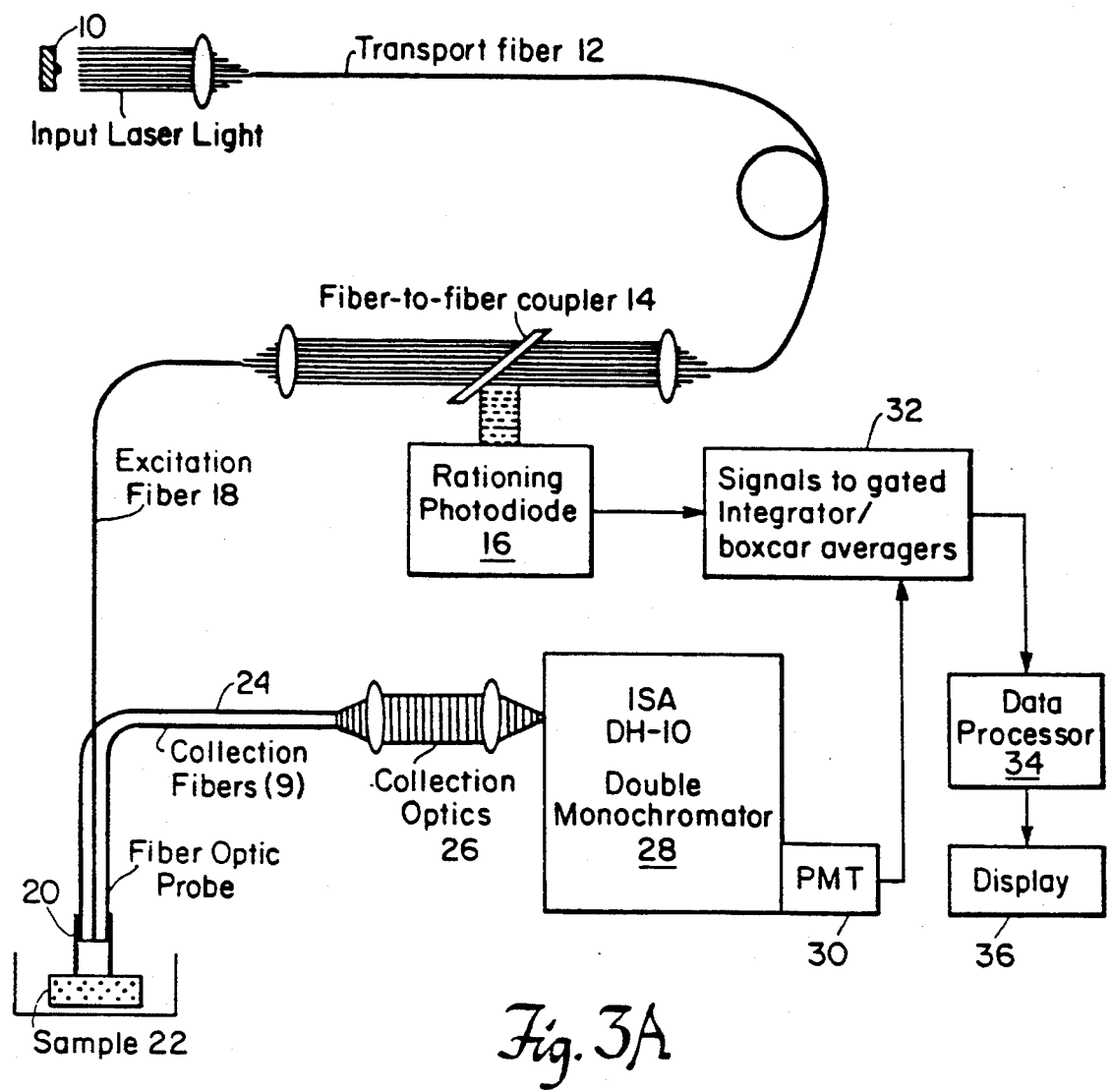
Figure 3B:
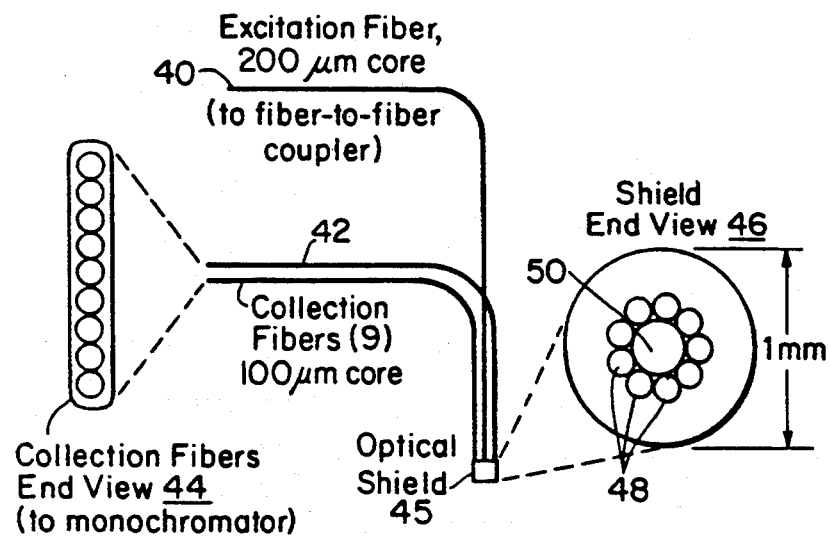
Figure 4:
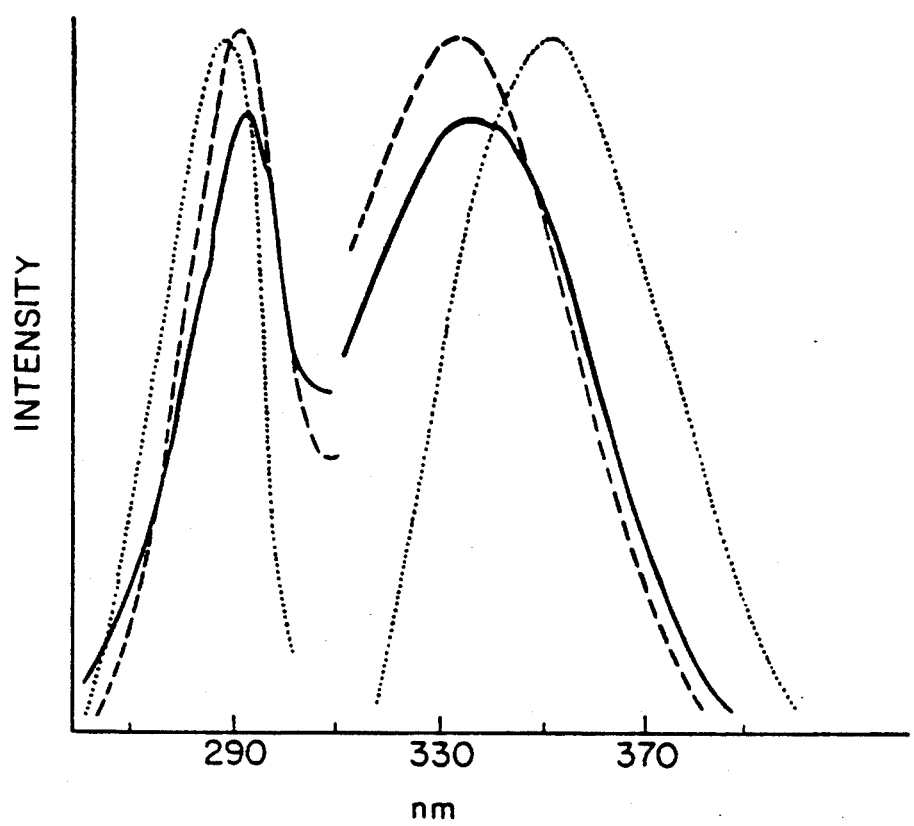
FIG. 4 graphically illustrates excitation and emission profiles of tryptophan ($10^{-5}$M)( ..... ), S. epidermidis (-----), and E. coli (-----). The excitation scans were obtained with $\lambda_{em}=340$ nm and the emission scans were obtained with $\lambda_{ex}=290$ nm. Note that the intensity scale has been arbitrarily adjusted.

A preferred embodiment of a probe used for laser induced fluorescence of tissue is shown in FIG. 3B in which samples were excited and collected through a fiber optic probe. The distal end of this probe consists of a center 200 $\mu$m fused silica core excitation fiber and nine surrounding 100 $\mu$m fused silica core collection fibers arranged in a close-packed circular array. A fused silica shield is bonded in front of the polished fiber ends, so that a constant excitation spot diameter (0.65 mm) is maintained on the shield output surface and the collection geometry is reproducible and well-defined. With this arrangement the fractional area of overlap of the excitation and collection spots is calculated to be about 0.71. This high degree of overlap is important, as LIF tissue experiments in the visible have shown that fluorescence reabsoption effects are enhanced in the collection regions not directly illuminated by the excitation light. At the proximal end of the device, the excitation fiber 18 is isolated from the collection fibers 24 and is connected to a fiber-to-fiber excitation coupler 14. The nine collection fibers are regrouped into a linear close-packed array and are optically Time Decay ultraviolet-excited LIF has been performed with the psec laser system using Time Correlated Photon Counting (TCPC). This method can determine fluorescence decay times with resolution of 30–100 psec. It is also good for poor fluorophores; being a photon counting system, it is designed to work well with weak signals. In fact, strong signals can require attenuation. The TCPC method has become well known and needs no further description.

Figure 10:
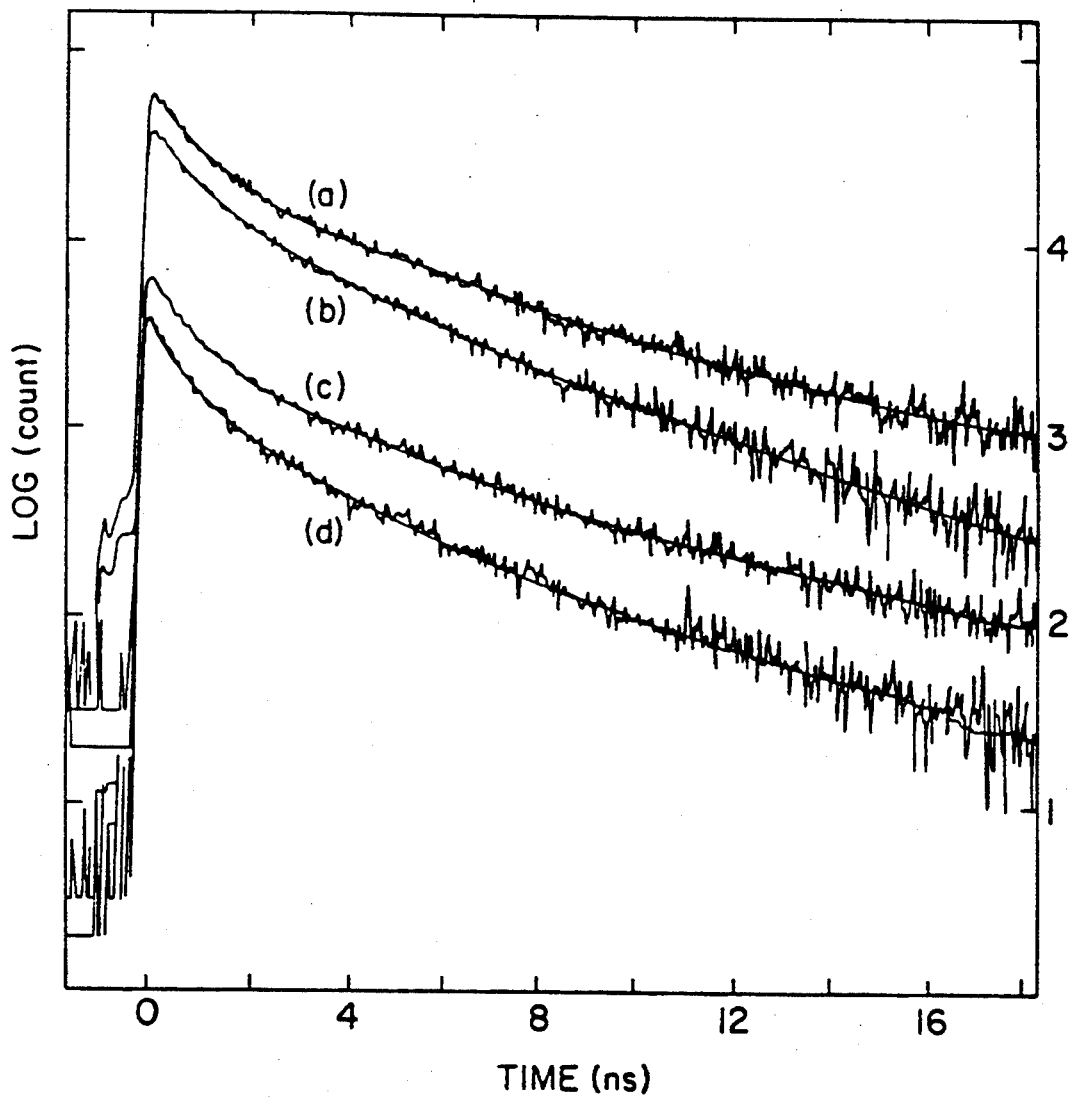
FIG. 10 is a graphical illustration plotting fluorescence decay curves of human aorta at (a) 305 nm excitation and 440 nm emission, (b) 305 nm excitation and 350 nm emission, (c) 310 nm excitation and 440 nm emission and (d) 310 nm excitation and 350 nm emission. The curves have been offset relative to one another.
Figure 11:
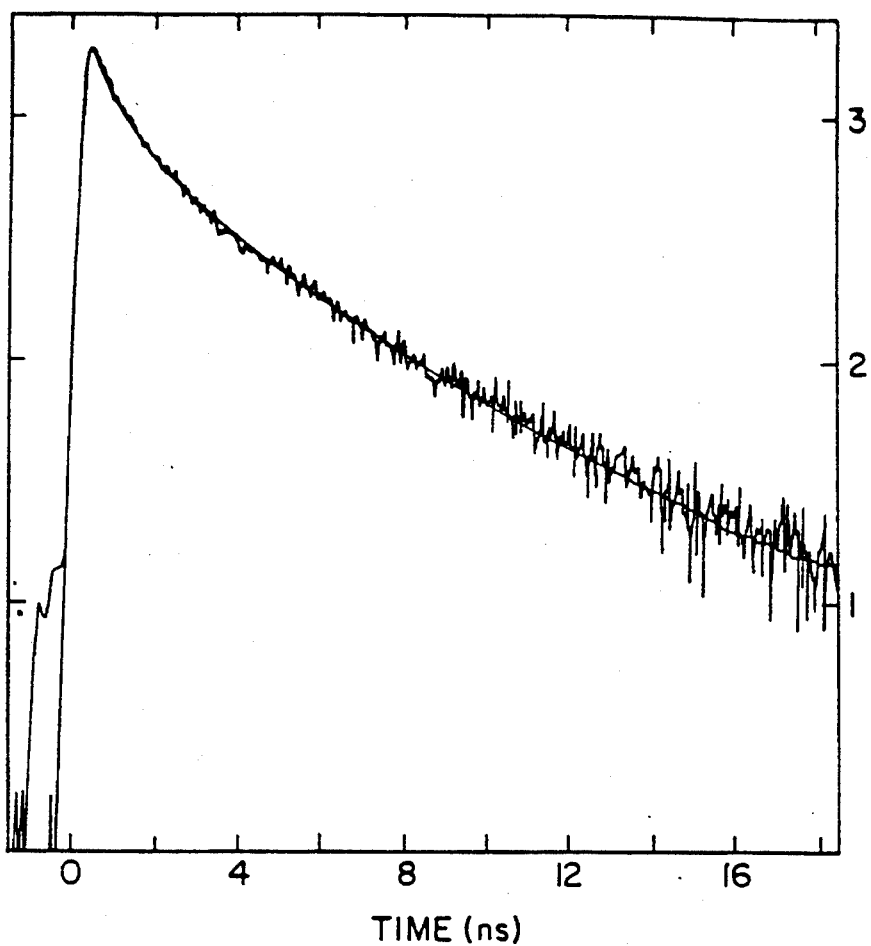
FIG. 11 is a graphical illustration of a fit of the fluorescence decay of human aorta at 305 nm excitation and 350 nm emission.

The fluorescence time decay of human aorta excited in the same range referenced above was measured at 350 and 440 nm, wavelengths at which the emissions of the two fluorophores are well separated. At 305 nm excitation and 350 nm emission, the shorter wavelength fluorophore dominates the fluorescence; at 310 nm excitation and 440 nm emission, the longer wavelength fluorophore prevails. FIG. 10 shows time decays at 305 and 310 nm excitations. Both decays are similar at the two excitations; however, the 350 nm emission decays somewhat faster than the emission at 440 nm.

Figure 12A:
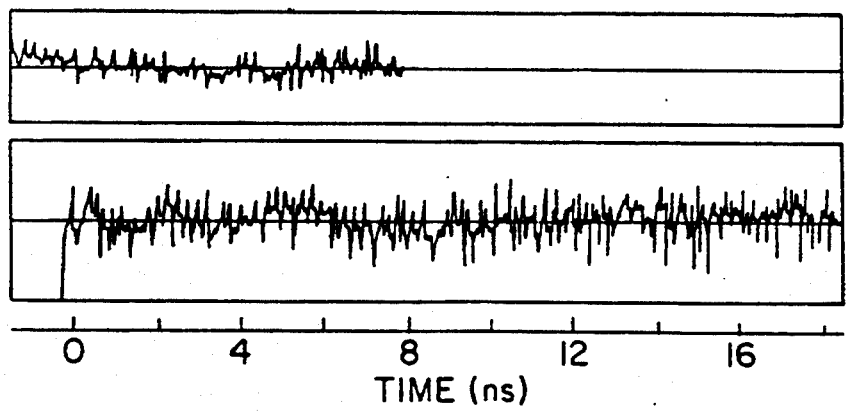
FIGS. 12A and 12B are the autocorrelation of the residuals ($\pm 0.3$ full scale) and the weighted residuals ($\pm 5$ full scale) for a three exponential fit ($x^2=1.15$) (at 12A) and the same curves for a four exponential fit ($x^2=1.08$) (at 12B). The residuals for three and four exponentials are similar, however, the autocorrelation for three exponentials shows a long range deviation, indicating a poor fit, while the autocorrelation for four exponentials shows no such deviation, indicating a good fit.
Figure 12B:
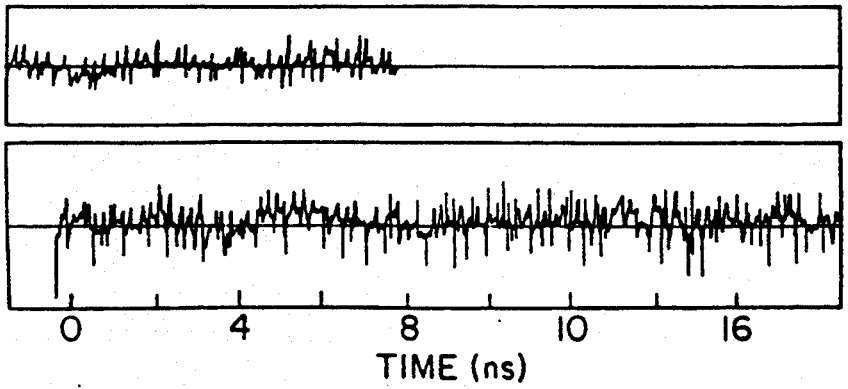

In order to extract information from the time-resolved decays, the decay curves were fit to a sum of exponentials in the form $K(t) = A_1 \exp(-t/\tau_1) + A_2 \exp(-t/\tau_2) + \ldots$ Deconvolution analysis was done by an iterative reconvolution method with parameter adjustment by the Marquardt procedure. The quality of the fit was judged by visual inspection of the autocorrelation function of residuals, the weighted residuals, and by $\chi^2$. In the present embodiment, the measured decays could not be fit with two or three exponentials, as indicated by the drift in the autocorrelation function (FIG. 12A). A minimum of four exponentials was needed to obtain a good fit (FIG. 12B); an attempt to a fifth exponential did not improve the fit for this particular analysis.

The 350 nm emission excited with 305 nm decayed with time constants of 0.003(0.73), 0.65(0.14), 2.1(0.070), and 4.9(0.058). (All time constants $\tau$ are reported in nanoseconds, and their corresponding normalized amplitudes A appear in parentheses.) The 440 nm emission with 310 nm excitation yielded time constants of 0.071(0.52), 0.61(0.29), 2.95(0.14), 8.6(0.052). With both excitations, the last two time constants are longer at 440 nm emission compared with emission at 350 nm. One possible explanation is energy transfer to the longer wavelength fluorophore. A short decay component emerges in both fits; however, with resolution (40 ps) and response time (150 ps), it cannot be concluded that the values (33 ps and 71 ps) are distinct. Scattered laser light is rejected as a possibility for this fast component, as a cutoff filter eliminates this source of light. A similar short lifetime component has been observed in fluorescence decay of tryptophan in several different proteins, which has been attributed fast energy transfer.

As discussed above, the fluorescence at 350 nm excited by 305 nm is due to tryptophan. Tryptophan fluorescence in solution has two exponentially decaying components with time constants of 0.6 and 2.5 ns. Longer decay constants for tryptophan fluorescence have been observed in other environments. The three long time decay constants of 0.65, 2.1 and 4.9 ns are in the correct range for the known values of tryptophan lifetimes in different environments.

As discussed above, tryptophan is an efficient fluorescing moiety in tissue; in fact it will totally dominate if excited at its absorption peak at 280 nm. However, by carefully choosing the excitation wavelength, about 310 nm, the tryptophan absorption cross-section is much smaller and the emission does not overwhelm much weaker fluorescing chromophores. Therefore, tissues containing relatively more tryptophan (normal vs. plaque) will have more of this efficient chromophore. But efficient fluorescence means that other competing non-radiative depopulating processes are less effective than for weakly emitting chromophores. Since the non-radiative decay processes rather than radiative processes generally dominate the population removal, the excited state for an efficiently emitting chromophore will live longer, yielding a longer fluorescence lifetime. Proportionally higher tryptophan content will lengthen the observed tissue lifetime.

There are other wavelengths of interest: 365 nm excites AND/NADH; are 400 nm excites blue-emitting chromophores, and 470 nm excites the 500–620 nm chromophores. Similar lifetimes for the various "peaks" confirms the hypothesis of a single fluorescing chromophore which is given structure by hemoglobin reabsorption in bulk tissue. Dissimilar lifetimes would indicate more than one overlapping chromophore emission spectra. Non-exponential decays tend to indicate this also, although one chromophore in two different environments can also be bi-exponential. Changing excitation wavelength helps here; as has already been demonstrated for ultraviolet tissue spectroscopy, the chromophore fluorescence is enhanced or inhibited relative to another.

To reiterate, LIF measurements of human artery wall indicate that at least two distinct fluorophores are being excited in aorta in the 305 to 310 nm region. The structural proteins collagen and elastin, via similar cross-linking agents, are probably responsible in large part for the longer wavelength fluorescence. The shorter wavelength fluorescence is attributed to tryptophan.

The present procedure establishes the ability to spectroscopically observe two or more fluorophores and determine relative contributions to the spectrum. The spectral lineshape is very sensitive to excitation wavelengths near the absorption edge. For example, tryptophan shows such sensitivity between 305 and 310 nm, the relative contributions of each fluorophore to the overall spectrum can be precisely controlled. Either fluorophore can be emphasized to aid in diagnosis by simply tuning the excitation wavelength a few nanometers; in addition, two or more fluorophores can be simultaneously observed by an appropriate choice of excitation wavelength and the ratio of emitted peaks can be adjusted for optimal comparison. This control is very important in identifying the chromophores and, hence, diagnosing the tissue type and condition for all kinds of bodily tissue. Differences in relative concentrations of the molecules, for instance in normal and diseased arteries, can be spectroscopically monitored; in addition, such relative measurements are both easier to perform and less sensitive to uncertainties in collection efficiency compared to absolute measurements.

LIF spectral signatures of arterial tissues have been observed using ultraviolet excitation. Excitation wavelength is critical to the spectral signatures, and selection of the wavelength has a basis in knowledge of the composition of the tissue. Spectral emission can therefore be tailored by selecting the excitation wavelength to enhance differences. Individual tissue components and localized laser damage may be studied microscopically. Spectral "tours" of the thin sections can help determine the individual contributions to the bulk tissue spectra which will help generate a physical and chemical basis for understanding the LIF spectral fingerprint of bulk tissue. Photochemically induced changes in spectra reflect changes in the oxidation stage of native compounds. Picosecond time resolved measurements will aid in this understanding. This is of general applicability and should be readily adapted for studying cancerous and other diseased and healthy tissue.

The following relates to a general method of extracting clinical information about tissue type, degree of disease, and physicochemical composition from tissue fluorescence spectra, utilizing a general model of tissue fluorescence. Our approach, which is based on a single-layer method analyzing of tissue fluorescence, includes contributions from intrinsic fluorescence, scattering and absorption from individual tissue components. In principle, as this physicochemical information is intimately related to the pathologic state of the tissue, the method should provide more precise diagnostic criteria than empirical methods.

As a specific example of this general method, the 476 nm laser induced fluorescence (LIF) spectra of human artery wall of 148 samples from 30 autopsy sources has been analyzed. The utility of empirical methods and the present method based on a general diagnostic is compared. In addition the extracted parameters are procedure correlated to the chemical composition of the tissue. The results demonstrate that the method characterizes the chemical composition of the tissue, and can be used to classify the pathology of the tissue.

In the following embodiment the one layer method of tissue fluorescence is presented and applied to human artery wall. The apparatus used to obtain tissue LIF spectra has been presented earlier. Thus the following outlines the procedures utilized to extract fluorescence and attenuation lineshapes for the chromophores of arterial tissue. Application of the method to different arterial tissue types is demonstrated and the results are summarized. The extracted parameters are correlated to the chemical composition of artery and the use of the method for diagnosing different stages of atherosclerosis in terms of sensitivity, specificity and predictive value are presented.

In the present general method, tissue is represented as a single layer, which is infinitely thick with respect to the penetration depth of the irradiating light. This proposition is most appropriate for excitation wavelengths for which 1/e of the penetration depth is less than the thickness of the top layer. In addition for the present method light is attenuated exponentially in tissue, due to absorption and scattering. In describing this attenuation, scattering and absorption are not treated separately but are considered together as total attenuation. For this method, chromophores are distributed homogeneously in the tissue and the excitation beam is assumed to be uniform in profile and infinitely wide.

Edge effects are neglected thereby restricting the method to a single dimension, namely, depth into the tissue. The composite tissue fluorescence power arriving at the $S(\lambda_x, \lambda_m)$, which is a function of both the excitation $(\lambda_x)$ and emission $(\lambda_m)$ wavelength can then be written as:

$$S(\lambda_x,\lambda_m) = k \underbrace{\int_0^\infty P(\lambda_x) e^{-\mu_t(\lambda_x)z}}_{A} \underbrace{\mu_a(\lambda_x) \frac{\phi(\lambda_x,\lambda_m)}{2}}_{B} \underbrace{e^{-\mu_t(\lambda_m)z} dz}_{C} \quad (1)$$

Due to scattering, the maximum intensity just below the tissue surface is higher than the incident intensity. This effect is included in Eq. (1) as k, a proportionality factor which depends on the tissue index of refraction and the incident wavelength, and also contains the detector efficiency. $P(\lambda_x)$ denotes the incident excitation power, $\mu_t(\lambda)$ and $\mu_a(\lambda)$, in units of length $^{-1}$, are the total attenuation and absorption coefficients of the tissue, respectively. $\phi(\lambda_x,\lambda_m)$ is the quantum yield of fluorescence, defined as the total fluorescence energy emitted at $\lambda_m$ over the total absorbed energy at $\lambda_x$, and z is the distance from the irradiated surface.

Equation (1) has a simple physical interpretation. Term A represents the attenuation of the incident radiation; term B represents the conversion of this light into backward directed fluorescence; and term C represents the attenuation of this net backward directed fluorescence. On average, assuming isotropic emission of fluorescence, the net backward directed fluorescence is half that of the total net fluorescence, resulting in the factor of 2 in term B.

Integrating Eq. (1) yields:

$$S(\lambda_x,\lambda_m) = \frac{kP(\lambda_x) \mu_a(\lambda_x) \frac{\phi(\lambda_x,\lambda_m)}{2}}{(\mu_t(\lambda_x) + \mu_t(\lambda_m))} \quad (2)$$

The quantities $\mu_a\phi$ and $\mu_t$ contain contributions from all of the individual tissue chromophores. It is this information which requires separation. Thus, a more useful way to write Eq. (2) is to express $\mu_a\phi$ and $\mu_t$ as sums over the N chromophores:

$$S(\lambda_x,\lambda_m) = kP(\lambda_x) \frac{\sum_{i=1}^{N} \mu_{ai}(\lambda_x) \frac{\phi_i(\lambda_x,\lambda_m)}{2}}{\sum_{i=1}^{N} (\mu_{ti}(\lambda_x) + \mu_{ti}(\lambda_m))} \quad (3)$$

The method has been applied to a specific system; the LIF of human cadaver aorta excited at 476 nm. Human aorta is composed of three layers. In normal tissue, the luminal layer, intima, is comprised of an endothelial layer, a few collagen fibers and some fibroblasts. The second layer, media, is made up mainly of elastin and some smooth muscle cells. The outer layer, adventitia, is comprised of loose connective tissue.

Different stages in the progression of atherosclerosis, summarized in Table 1, are classified by the chemical and physical changes which occur within the intimal layer.

The first stage, intimal fibroplasia (1), is characterized initially by intimal proliferation of smooth muscle cells and fibroblasts. In well developed

TABLE 1

| Category | Tissue Type | Intimal Morphology |
|---|---|---|
| 0 | Normal | Endothelial layer Some collagen Some fibroblasts |
| 1 | Intimal Fibroplasia | Smooth muscle cell proliferation Collagen accumulation |
| 2 | Atherosclerotic | Collagen proliferation Invasion of lipids and foam cells |
| 3 | Atheromatous | Collagen proliferation Formation of necrotic core |
| 4 | Calcified Atherosclerotic | Atherosclerotic + Calcifications |
| 5 | Calcified Atheromatous | Atheromatous + Calcifications |
| 6 | Fibrotic/ Sclerotic | Dense collagen proliferation |

TABLE 1-continued

| Category | Tissue Type | Intimal Morphology |
|---|---|---|
| | | Loss of lipids | intimal fibroplasia, collagen accumulates. An atherosclerotic plaque (2) is indicated when the intima is infiltrated by lipids and foam cells. When the center of the plaque becomes necrotic, the plaque is characterized as atheromatous (3). Both atherosclerotic and atheromatous plaques can develop significant calcifications, and are then classified as calcified atherosclerotic (4) and calcified atheromatous (5) plaques respectively. Fibrotic/sclerotic lesions (6) are end stage plaques, characterized by intimal sclerosis with loss of lipid and foam cells.

476 nm laser induced fluorescence microscopy of normal tissue and the types of atherosclerotic plaques described previously has shown that the important fluorophores are those listed in Table 2.

TABLE 2

| 0,1 | 2,3 | 4,5 | 6 |
|---|---|---|---|
| Fluorophores: | | | |
| Collagen | Collagen | Collagen | Collagen |
| Elastin | Elastin | Elastin | Elastin |
| | Ceroid | Ceroid | |
| Attenuators: | | | |
| Collagen | Collagen | Collagen | Collagen |
| Elastin | Elastin | Elastin | Elastin |
| Hemoglobin | Hemoglobin | Hemoglobin | Hemoglobin |

In normal tissue, fluorophores in or associated with the structural proteins (SP), collagen and elastin, are important. Fluorescence contributions from collagen and elastin are not treated separately below, as these compounds have identical fluorescence lineshapes with 476 nm excitation. In atherosclerotic tissue, ceroid (Ce) contributes to the fluorescence in addition to the structural proteins, as detailed in Table 2. Ceroid is a morphologic term used to denote substances which (i) stain like a lipid, (ii) are not dissolved by usual lipid solvents, and (iii) fluoresce in the visible when excited by UV light. Ceroid is a complex of protein associated with oxidized lipids and its exact identity is unknown.

The attenuation effects of ceroid and the structural proteins are included in equation (3). In addition, as noted above absorption spectroscopy indicates that hemoglobin (Hb) is an important attenuator in normal and atherosclerotic tissues. Using this information, the most general form of eq. (3) including all of these chromophores is:

$$S(476,\lambda_m) = \qquad (4)$$

$$kP(476)\left\{ \mu_{aSP}(476)\frac{\phi_{SP}(476,\lambda_m)}{2} + \mu_{aCe}(476)\frac{\phi_{Ce}(476,\lambda_m)}{2} + \mu_{aHb}(476)\frac{\phi_{Hb}(476,\lambda_m)}{2} \right\} /$$

$$\{(\mu_{tSP}(476) + \mu_{tSP}(\lambda_m)) + (\mu_{tCe}(476) + \mu_{tCe}(\lambda_m)) + (\mu_{tHb}(476) + \mu_{tHb}(\lambda_m))\}$$

A knowledge of the chemical properties of these chromophores and the physical structure of arterial tissue allows us to simplify Eq. (4). First, the quantum efficiency of hemoglobin is negligible. Second, fluorescence microscopy shows that ceroid is present as small discrete deposits near the central necrotic region of plaques. The implications of this can be most easily seen if equation (4) is written as:

$$S(476,\lambda_m) = \qquad (5)$$

$$kP(476)\left\{ \frac{\mu_{aSP}(476)\frac{\phi_{SP}(476,\lambda_m)}{2}}{[\mu_{tSP}(476) + \mu_{tSP}(\lambda_m) + \mu_{tHb}(476) + \mu_{tHb}(\lambda_m) + \mu_{tCe}(476) + \mu_{tCe}(\lambda_m)]} + \right.$$

$$\left. \frac{\mu_{aCe}(476)\frac{\phi_{Ce}(476,\lambda_m)}{2}}{[\mu_{tSP}(476) + \mu_{tSP}(\lambda_m) + \mu_{tHb}(476) + \mu_{tHb}(\lambda_m) + \mu_{tCe}(476) + \mu_{tCe}(\lambda_m)]} \right\}$$

The localization of ceroid implies that the attenuation of structural protein fluorescence by ceroid is small; therefore, the ceroid attenuation terms can be neglected in the denominator of the first term in eq. (5). Although the effects of ceroid attenuation can be neglected for structural protein fluorescence, they are important for ceroid fluorescence. These effects in an approximate way. The ceroid attenuation terms in the denominator of the second term in eq. (5) are neglected, but the ceroid fluorescence term in the numerator is replaced with an effective ceroid fluorescence lineshape. This lineshape is approximated as the intrinsic fluorescence lineshape divided by a normalized ceroid attenuation lineshape. Eq. (5) can be rewritten to reflect these considerations as:

$$S(476,\lambda_m) = \frac{kP(476)\left\{ \mu_{aSP}(476)\frac{\phi_{SP}(476,\lambda_m)}{2} + \frac{\mu_{aCe}(476)}{\frac{\mu_{tCe}(476) + \mu_{tCe}(\lambda_m)}{\mu_{tCe}(476) + \mu_{tCeMax}}} \frac{\phi_{Ce}(476,\lambda_m)}{2} \right\}}{\{(\mu_{tSP}(476) + \mu_{tSP}(\lambda_m)) + (\mu_{tHb}(476) + \mu_{tHb}(\lambda_m))\}} \qquad (6)$$

In eq. (6) $\mu_{tCeMax}$ is the maxiumum ceroid attenuation coefficient over the emission wavelength range. As discussed above, the modulation of ceroid fluorescence by ceroid attenuation is included by dividing the ceroid fluorescence by a normalized ceroid attenuation lineshape. This represents a relaxation of the assumption that ceroid is distributed homogeneously, in order to better reflect the physical situation. This approximation allows the ceroid fluorescence lineshape to be extracted from bulk samples (samples thick with respect to the penetration depth of the excitation light), eliminating difficulties which would be associated with obtaining an unattenuated ceroid fluorescence lineshape.

Eq. (6) can be simplified further if the fluorescence and attenuation lineshapes are normalized yield:

$$S(476,\lambda_m) = \qquad (7)$$

-continued $$\frac{kF(476)\{\beta_{SP}(476) F_{SP}(476,\lambda_m) + \beta_{Ce}(476) F_{Ce}(476,\lambda_m)\}}{\{x_{SP}(476) A_{SP}(476,\lambda_m) + x_{Hb}(476) A_{Hb}(476,\lambda_m)\}}$$

where $$\beta(476) = \frac{\mu_a(476) \phi_{Max}}{2} \quad (8)$$

$$F(476,\lambda_m) = \frac{\phi(476,\lambda_m)}{\phi_{Max}}$$

$$x(476) = \mu_r(476) + \mu_{tMax}$$

$$A(476,\lambda_m) = \frac{\mu_r(476) + \mu_r(\lambda_m)}{\mu_r(476) + \mu_{tMax}}$$

$$\beta = \frac{\mu_a(476) \phi_{Max}}{2}$$

$$F = \left[\frac{\frac{\phi(476,\lambda_m)}{\mu_r(476) + \mu_r(\lambda_m)}}{\mu_r(476) + \mu_{tMax}}\right]\left[\frac{1}{\phi_{Max}}\right] = \frac{\phi(476,\lambda_m)}{\phi_{Max}}$$

In Eq. (8), $\phi_{Max}$ and $\mu_{tMax}$ are the maximum quantum yield and the attenuation coefficient over the emission wavelength range, respectively. F represents a normalized intrinsic fluorescence lineshape and A represents a normalized round trip attenuation lineshape. As $\mu$ is proportional to the chromophore concentration, both $\beta$ and x are proportional to the chromophore concentration. In addition, $\beta$ is proportional to the quantum yield at the peak emission wavelength. Thus, changes in $\beta$ can reflect either changes in the chromophore concentration or quantum yield.

In our treatment of ceroid, $\phi_{Max}$ and $\mu_{tMax}$ are the maxiumum yield and attenuation coefficient over the emission wavelength range, respectively. F represents a normalized intrinsic fluorescence lineshape and A represents a normalized round trip attenuation lineshape. As $\mu$ is proportional to the chromophore concentration, both $\beta$ and x are proportional to the chromophore concentration. In addition, $\beta$ is proportional to the quantum yield at the peak emission wavelength. Thus, changes in $\beta$ can reflect either changes in the chromophore concentration or quantum yield.

In our treatment of ceroid, $\phi$ if replaced by $\phi'$; $\phi'$ represents an effective quantum yield for the net ceroid fluorescence which has been modulated by ceroid absorption. Thus $\beta'_{Ce}$ is proportional to the ceroid concentration and its maximum effective quantum yield. $F_{Ce}$ is the normalized fluorescence lineshape from a sample thick compared to the penetration depth of 476 nm radiation.

Eq. (7) is the key equation to understanding the fluorescence from artery wall. It shows that the fluorescence from both the structural proteins and ceroid are modulated by attenuation of the structural proteins and hemoglobin. Ceroid fluorescence is also modulated by ceroid attenuation. In the following description the lineshapes needed to utilize Eq. (7) are extracted using fluorescence spectra of optically thick tissues.

Generally, the apparatus used to collect the tissue fluorescence spectra of FIGS. 13-17 is illustrated in FIGS. 3A-3D and consists of an argon ion laser 10, an optical fiber laser catheter or probe 20, and a scanning monochromator 28 with a photomultiplier tube 30. One embodiment of an optical fiber laser catheter used to collect data contains nine optical fibers 24 encased in a transparent quartz shield 45 the fibers 24 concentric around a central excitation fiber 18, coupled to the laser, which in this embodiment provides a 1 mm diameter spot at the surface of the shield. The collection fibers 24, surrounding the central fiber 18 are arranged to view only the tissue illuminated by the central fiber, and are used to collect tissue fluorescence. The distal ends 48 of these fibers are coupled to the entrance slits of the monochromator 28 with suitable collection optics 26. FIG. 3B shows the distal end 46 of the probe where the distal ends 50,48 of the excitation and collection fibers respectively are concentrically arranged. FIGS. 3C and 3D show an alternative embodiment using a larger number of fibers 52 concentric around a central lumen 58 and coupled to an optical shield 56 having a distal surface 60 on which overlapping spots of light 62 are formed.

The data from the photomultiplier tube 30 can be averaged with the use of signals from the ratioing photodiode 16 and subsequently processed 34 and displayed 36.

The well defined collection geometry of this system represents a substantial improvement over that of typical spectrofluorimeters, in which recorded signals are significantly distorted by reabsorption. In collecting tissue fluorescence spectra, an excitation intensity of 100 $\mu W/mm^2$ was used in a 1.0 mm diameter spot. Data collection time was 40 seconds. Spectral resolution of the detector was 6 nm FWHM, and a time constant of 250 ms was used to record all data. Data presented has been corrected for the non-uniform spectral response of this system.

All tissue studied was human cadaveric aorta obtained at autopsy within 24 hours of expiration. Samples were snap-frozen in liquid nitrogen and isopentane and then stored at $-70°$ C. until use. Spectra were obtained from samples kept moist using a buffered, isotonic saline solution, pH 7.4, at room temperature. Tissue type was determined histologically according to Table 1.

In order to fix the lineshapes in Eq. (7), several simple one-layer arterial tissue systems were studied, as opposed to studying the optical properties of pure chromophores. The advantage of this approach is that it intrinsically includes the effects of scattering in the tissue. In addition, this method allows us to investigate endogenous chromophores in their natural environment, avoiding possible effects due to extraction.

In other cases, the composite spectrum will arise from two (or conceivalby three) layers; a one layer model will then describe the tissue in terms of some average of its optical properties. The extension to more than one layer is straightforward.

Flavins which have broad absorption at 450 nm and broad emission at 450 nm can also contribute to the fluorescence. The chromophores also contribute to the composite tissue fluorescence spectrum through reabsorption. A heme containing compound, believed to be oxy-hemoglobin, is also present mainly in the intima of normal aorta, but is found in lesser concentrations in media and atherosclerotic intima as well. The 540 and 580 nm absorption peaks of oxy-hemoglobin produce the valleys at 540 and 580 nm in the composite tissue fluorescence spectra.

Figure 13:
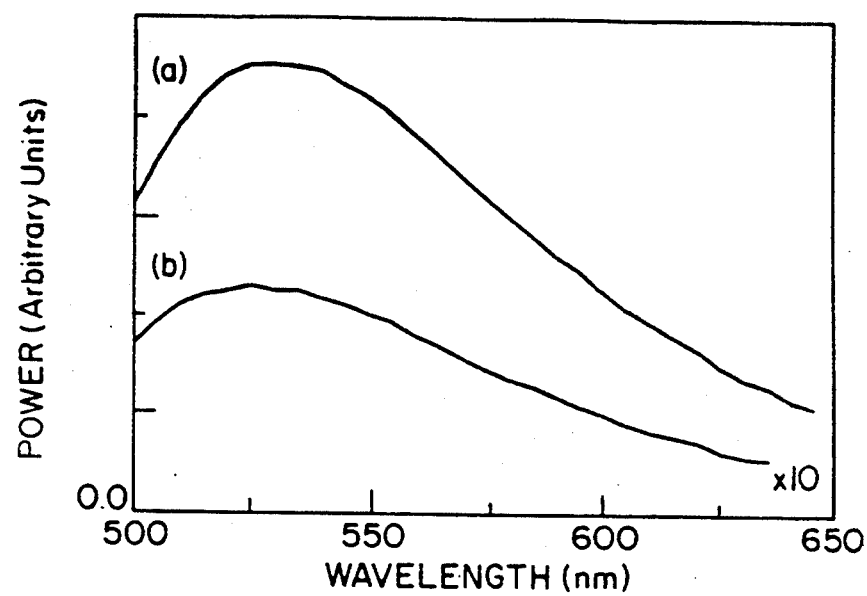
FIG. 13 is a graphical illustration of the emission spectrum (a) of bulk normal aorta excited at 476 nm and the product $\beta_{SP}(476) F_{SP}(476)$ dz(b).

The first system utilized a single optically thick section of media, blunt dissected from a sample of normal aorta. A fluorescence spectrum of the bulk tissue was recorded yielding $S(476\lambda_m)$ and is shown in FIG. 13.

The 476 nm excited fluorescence lineshape of media is found to be identical to that of powdered bovine collagen and elastin. In addition, the fluorescence spectrum of this section of media did not exhibit valleys at 540 and 580 nm, which have been attributed to the presence of hemoglobin. Thus, the important chromophores in this system are limited to structural proteins, but the use of the present procedures is not limited to these proteins. Eq. (7) simplifies to $$S(476,\lambda_m) = \frac{\beta_{SP}(476) F_{SP}(476,\lambda_m)}{x_{SP}(476) A_{SP}(476,\lambda_m)} kP(476) \quad (9)$$

Figure 14:
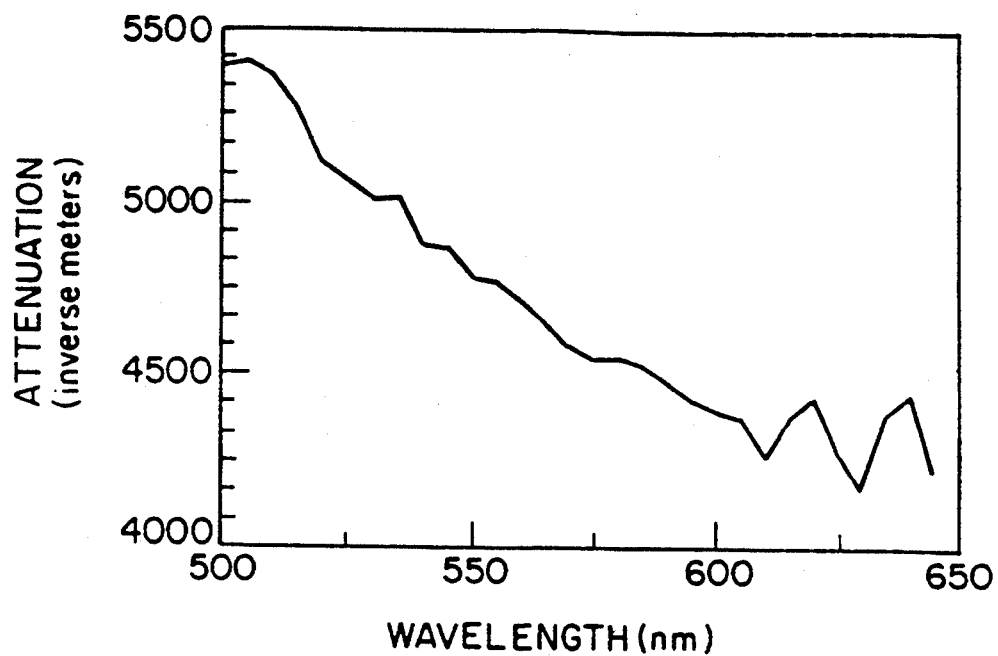
FIG. 14 graphically illustrates the attenuation lineshape $\chi_{SP}(476) A_{SP}(476, \lambda_m)$.
Figure 15:
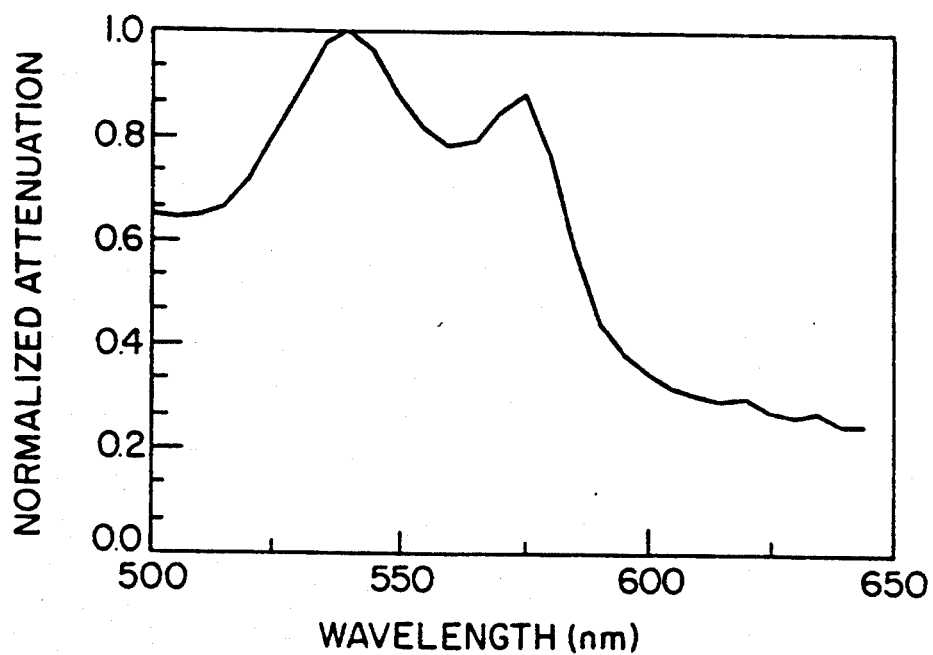
FIG. 15 graphically illustrates an average plot of several curves showing the normalized hemoglobin attenuation lineshape.

A fluorescence spectrum was then obtained from a 10 μm section of normal media directly providing an unattenuated structural protein emission, as $$S_{Thin}(476,\lambda_m) = \beta_{SP}(476) F_{SP}(476,\lambda_m) k\, P(476) dz \quad (10)$$

where dz is the sample thickness. $\beta_{SP}(476)F_{SP}(476)dz$ is also shown in FIG. 13. Thus $x_{SP}(476)A_{SP}(476,\lambda_m)$ can be extracted, and is shown in FIG. 14.

The next step was to obtain the hemoglobin attenuation lineshape, $x_{Hb}(476)A_{Hb}(476,\lambda_m)$. It has been shown that the hemoglobin content of tissue can be increased by exposing the tissue to hemolysed blood. We exploited this fact to extract the hemoglobin attenuation lineshape. The same thick section of media used above was exposed to hemolysed blood and a fluorescence spectrum of the bulk tissue was recorded. As hemoglobin is an important chromophore, Eq. (7) takes the form $$S(476,\lambda_m) = \frac{kP(476)\, \beta_{SP}(476)\, F_{SP}(476,\lambda_m)}{\{x_{SP}(476)\, A_{SP}(476,\lambda_m) + x_{Hb}(476)\, A_{Hb}(476,\lambda_m)\}} \quad (11)$$

Since $F_{SP}$ and $A_{SP}$ are known, $A_{Hb}$ can be extracted directly. Several $A_{Hb}$ curves were obtained for different concentrations ($x_{Hb}$) of hemoglobin corresponding to those typically observed in tissue in vitro, as judged by the depth of the valleys in the fluorescence spectrum at 540 and 580 nm. These curves were averaged, yielding the curve shown in FIG. 15.

Figure 16:
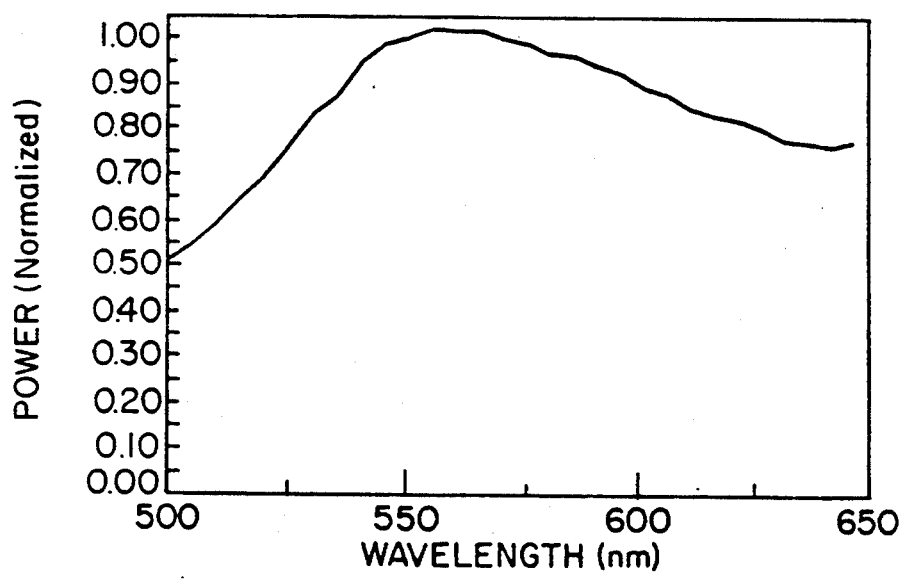
FIG. 16 is a graphical illustration of the normalized ceroid fluorescence lineshape measured from the bulk necrotic core of several fatty plaque specimens.

The only remaining lineshape in Eq. (7) is $F_{Ce}$. $F_{Ce}$ was measured directly from bulk necrotic core which was blunt dissected from specimens of fatty plaque. The localization of ceroid in the necrotic core permits this approach. The average lineshape from several samples is shown in FIG. 16.

Having determined the relevant lineshapes in Eq. (7, $F_{SP}$, $F_{Ce}$, $A_{SP}$ and $A_{Hb}$, the experimental LIF spectra from bulk tissue can now be modeled. The parameters in the model are $\beta_{SP}$ to vary while holding $x_{SP}$ constant, as $\beta_{SP}$ depends on the quantum yields, absorption coefficients and concentrations of collagen and elastin, while $x_{SP}$ depends on the attenuation coefficients and concentrations.

Figure 17:
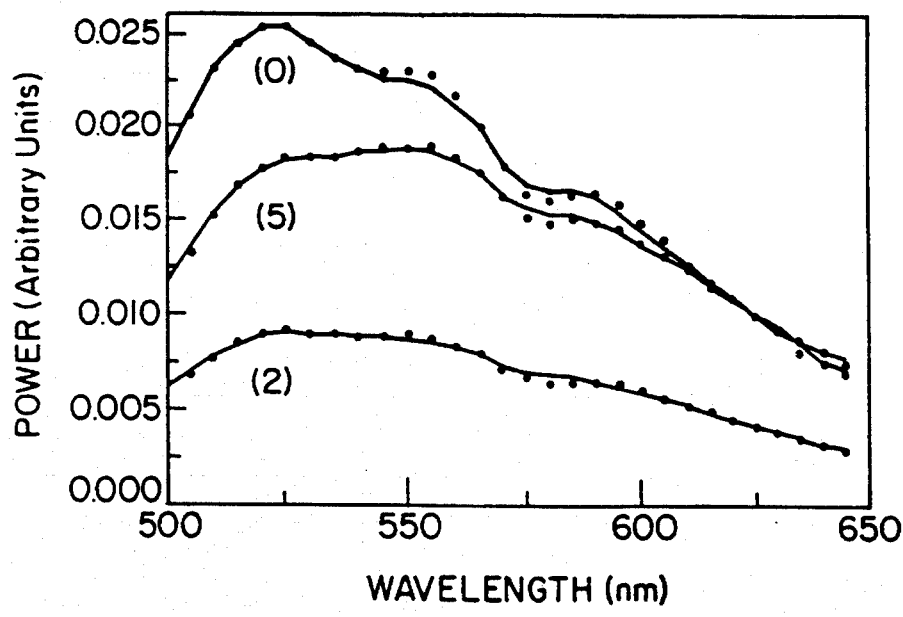
FIG. 17 graphically illustrates the correlation of actual fluorescence lineshapes for normal (0), calcified atheromatous (5) and atheroschrotic (2) sample with fluorescence lineshapes estimated by the disclosed procedure.

In fitting the data, the parameters were varied in order to minimize chi-square, the square of the difference between the experimental and calculated fluorescence signal divided by the standard deviation. Typical fits to data are shown in FIG. 17 for several different tissue types. The goodness-of-fit of the method to the data was judged by calculating the probability that a value of chi-square found in the calculation should occur by chance rather than due to an inappropriate procedure. This probability was calculated using an incomplete gamma function. In general, a probability of less than 0.1 for many samples would indicate that the procedure was a poor representation of the system. Typically, values of this probability for our data were found to be greater than 0.9. This shows that the procedure provides an adequate representation of arterial LIF spectra.

Figure 19:
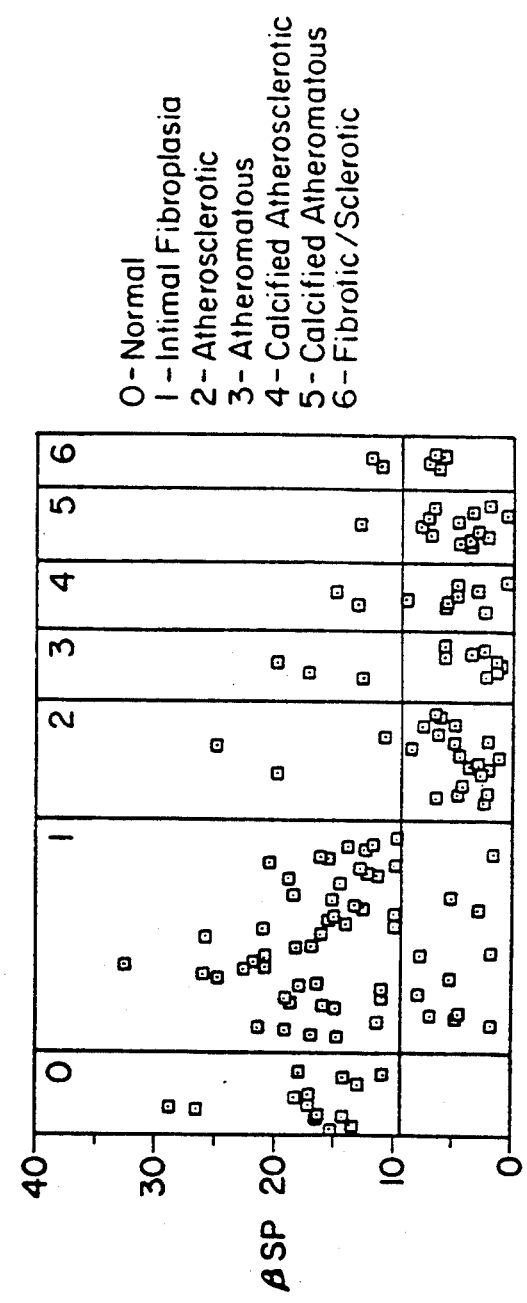
FIG. 19 is a scatter plot of $\beta_{SP}$ for the measured samples.

Scatter plots for each of the parameters, $\beta_{SP}$ $\beta'_{Ce}$ and $x_{Hb}$, for all samples are shown in FIGS. 19, 20, and 21, respectively. Table 3 lists averages and standard deviations for $\beta_{SP}$ and $\beta'_{Ce}$ for each of the classifications as well as some additional combinations of these classifications.

A "two-sided t test" was used to compare the parameters $\beta_{SP}$ and $\beta'_{Ce}$ for several different tissue classifications. $\beta_{SP}$ of (0.1) was significantly higher than that for pathologic tissues, (2,3), (4,5), with $p<0.01$. $\beta'_{Ce}$ for calcified tissues, (4,5) was significantly higher than that of other tissues: (0,1), with $p<0.01$ (2,3), with $p<0.10$. Interestingly, the values of $\beta_{SP}$ for (0) and (1) were not found to be significantly different, while the values of $\beta'_{Ce}$ were ($p<0.10$).

As shown in Eq. (7) the parameters of the model, $\beta$ and x, are directly proportional to the absorption and attenuation coefficients, respectively, and thus provide a link to the chemical composition of the tissue. As these coefficients are linearly related to the chromophore concentration, $\beta$ and x are proportional to the concentration. The proposition that there is a homogeneous distribution of chromophores is not rigorously true for multi-layered tissues in which the intimal thickness is less than the ⅓ of the penetration depth of 476 nm light in tissue. In applying a one layer method to a two layer system we calculate some average value of $\beta$ and x. These average values can vary, ranging from $\beta$ and x of layer two to that of layer one as the

TABLE 3

| Classification | No. of Samples | βSP | β'Ce |
|---|---|---|---|
| 0 | 16 | 16.95 ± 4.66 | 0.55 ± 0.91 |
| 1 | 58 | 14.28 ± 6.53 | 1.04 ± 0.96 |
| 2 | 25 | 5.90 ± 5.71 | 0.88 ± 0.78 |
| 3 | 11 | 6.41 ± 6.14 | 1.95 ± 1.95 |
| 4 | 10 | 6.35 ± 4.59 | 2.30 ± 2.77 |
| 5 | 14 | 4.94 + 3.11 | 2.11 ± 2.33 |
| 6 | 7 | 8.03 ± 2.50 | 0.03 ± 0.08 |
| 0,1 | 74 | 14.86 ± 6.25 | 0.94 ± 0.96 |
| 2,3 | 36 | 6.13 ± 5.79 | 1.26 ± 1.40 |
| 4,5 | 24 | 5.53 ± 3.77 | 2.19 ± 2.46 |

When measuring absolute fluorescence intensities, the information obtained is a combination of intrinsic fluorescence and attenuation. For example, a low value of absolute intensity can be due to either reduced intrinsic fluorescence or to increased attenuation. To obtain chemical information, it is necessary to separate these processes. In our method, the changing attenuation is due to the presence or absence of hemoglobin, as represented by the parameter $x_{Hb}$. As shown in FIG. 21, on average $x_{Hb}$ is higher for normal tissues. The distribution of values, however, overlaps widely with other tissue types. The usefulness of extracting $x_{Hb}$ lies in the ability to separate the effects of fluorescence and attenuation. In addition, in vivo measurements of arterial fluorescence have demonstrated that in vitro tissue may contain different concentrations of hemoglobin. In vivo measurements indicate that hemoglobin is not an important attenuator in normal tissue but is important in calcified plaques. Thus, the method in separating fluorescence and attenuation effects, provides a procedure for connecting in vivo and in vitro data.

A non zero $\beta'_{Ce}$ indicates the presence of ceroid. Ceroid has been correlated with the presence of extensive atherosclerosis. FIG. 20 and Table 3 show the data are consistant with this: the average value of $\beta'_{Ce}$ higher for pathologic specimens and appears to increase with the severity of the disease. Calcified plaques were associated with a particularly high value of $\beta'_{Ce}$. This is consistent with observations made with a fluorescence microscope indicating ceroid deposits are often localized adjacent to calcified areas of tissue. In fibrotic/sclerotic specimens, the amount of ceroid is negligible, reflecting the pathology of this tissue type. Detecting the presence of sub-surface ceroid fluorescence utilizing surface excitation is an important feature. The method provides a means of assessing ceroid content of tissues in vivo and in vitro.

Interpretation of the parameter $\beta_{SP}$ is complicated by the fact that $\beta_{SP}$ contains contributions from both collagen and elastin. Results indicate that the quantum efficiency of elastin is higher than that of collagen with 476 nm excitation, although the band shapes are identical. Thus, a high value of $\beta_{SP}$ indicates a high ratio of elastin concentration to collagen concentration. Since the media consists mainly of elastin, and the intima mainly collagen, the effective ratio of these concentrations, reflected by our one-layer value of $\beta_{SP}$, decreases as the intimal thickness increases. As shown in Table 3, $\beta_{SP}$ is highest for normal tissue, is slightly lower for intimal fibroplasia, and is significantly lower for pathologic specimens.

Although these results hold for comparing general classes of tissue, there are other important effects which also can influence $\beta_{SP}$. For example, in specimens displaying intimal fibroplasia there is no significant correlation of $\beta_{SP}$ to intimal thickness. This is due to the varying chemical structure of the intima as intimal fibroplasia develops. Initially, the intima is mostly cellular, but becomes collagenous with increasing intimal thickness. These higher concentrations of collagen can also lead to higher $\beta_{SP}$ values. In addition, it is known that the collagen structure can vary with tissue type and the presence or absence of atherosclerosis. Different collagens do not necessarily have the same quantum yield, and this factor can further affect $\beta_{SP}$.

The method parameters contain chemical information about tissue composition which is related to the presence of pathology in the tissue. The challenge in obtaining a clinical diagnostic is to find criteria which separate normal and pathologic tissue, despite the wide variance in the distributions of these parameters. For the purpose of this discussion, intimal fibroplasia is considered 'non-pathologic'. In the context of atherosclerosis, this classification is justified, since in the aorta intimal fibroplasia is rarely hemodynamically significant.

A simple criterion, $\beta_{SP} > 9.0$ indicating a non-pathologic (0,1) specimen and $\beta_{SP} < 9.0$ indicating pathology correctly diagnoses the presence or absence of atherosclerosis in 84% of the 148 samples shown in FIG. 19. This criterion, and others discussed below, were chosen to maximize the percentage of samples in which the presence or absence of atherosclerosis was correctly diagnosed. The $\beta_{SP}$ algorithm should be compared to a simple empirical diagnostic utilizing the intensity of 520 nm (FIG. 19). This empirical procedure is chosen because this wavelength corresponds to the fluorescence maximum observed for collagen and elastin, and thus should be related to $\beta_{SP}$. The empirical procedure correctly diagnoses 77% of the samples; however, it is particularly poor for calcified tissue (5,6), achieving a correct diagnosis in only 52% of the cases. The improvement in diagnosing calcified tissues in the method (88% correct) is largely due to the ability of the method to separate the effects of ceroid in $\beta'_{Ce}$ and those of collagen/elastin in $\beta_{SP}$. Neither $\beta_{Ce}$ nor $x_{Hb}$ alone were found to be useful in diagnosing tissue type.

Figure 18:
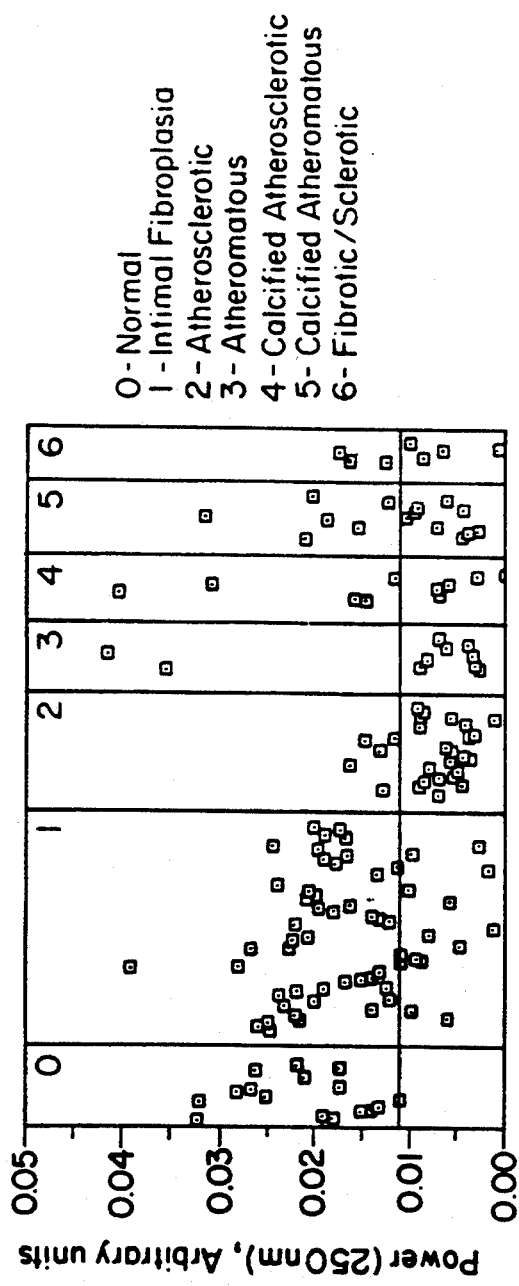
FIG. 18 is a scatter plot for an empirical procedure.

A better way to evaluate the efficacy of any procedure is to test its sensitivity, specificity and predictive value as defined in Eq. (12).

sensitivity = no. of true positives/total no. of diseased samples specificity = no. of true negatives/total no. of normal samples predictive value = no. of true positives/total no. of positives Here, positives refer to those samples diagnosed as having disease. True positives denote positives actually displaying disease, whereas, true negatives denote negatives which are actually normal. In general, the sensitivity measures the ability of the procedure to detect disease, while the specificity determines its ability to detect normal samples. The sensitivity, specificity and predictive value of the empirical procedure in FIG. 18 are 69%, 85% and 82%, respectively, which improved to 84%, 85% and 84% for the procedure shown for $\beta_{SP}$ in FIG. 19. The improvement in sensitivity reflects the ability of the $\beta_{SP}$ procedure to diagnose calcified samples.

Figure 22:
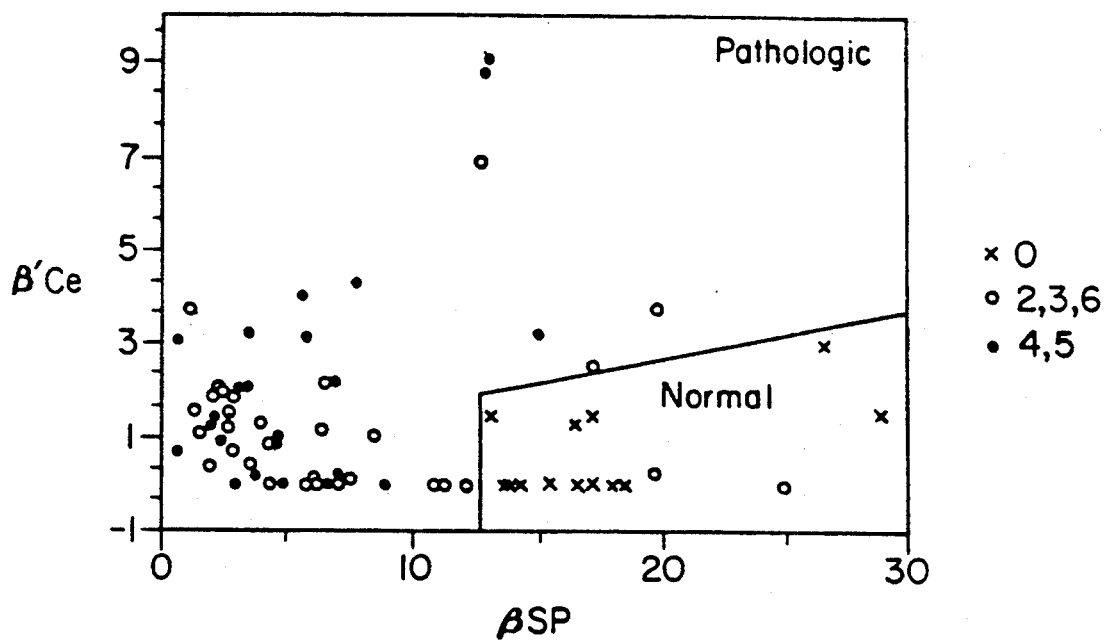
FIG. 22 is a graph of $\beta'_{Ce}$ versus $\beta_{SP}$ for all classifications except intimal fibroplasia.

In order to achieve more effective diagnosis, a binary classification scheme should be considered. FIG. 22 shows a plot of $\beta'_{Ce}$ vs $\beta_{SP}$ for all classifications except intimal fibroplasia. By limiting our consideration to these tissue categories, the sensitivity and specificity of binary schemes with respect to normal tissue (0), and normal and intimal fibroplasia (0,1) can be separately evaluated. The decision surface indicated by the divisions in FIG. 22 correctly diagnoses 98% of the samples. The sensitivity of this procedure to detect disease is 97%, while its specificity is 100%. The predictive value of this scheme is 100%.

Figure 23:
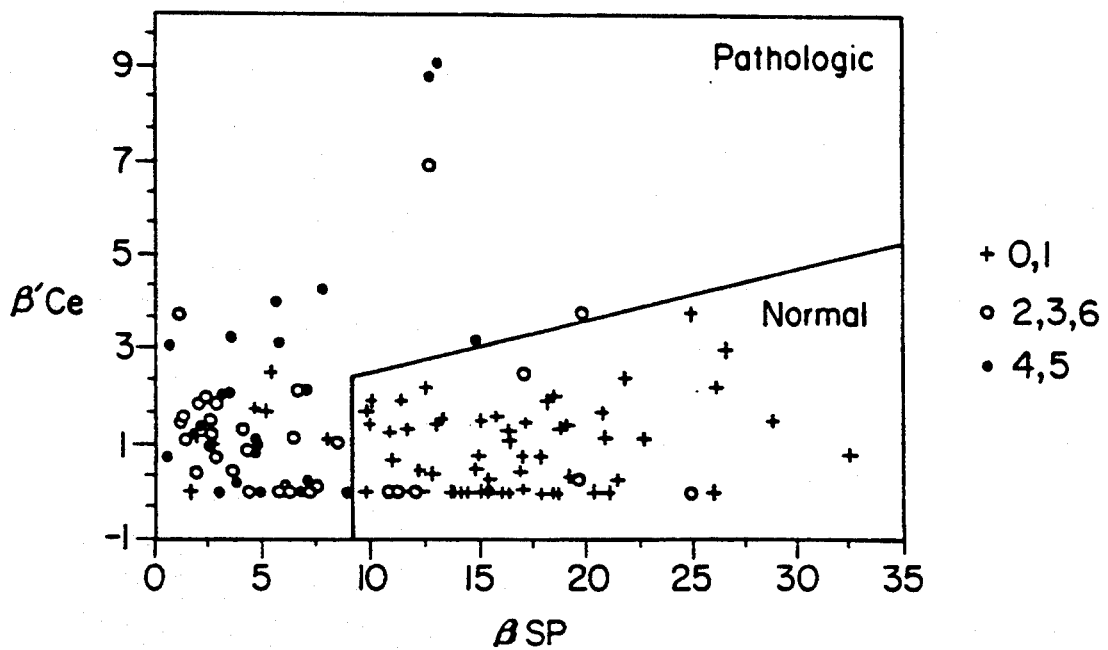
FIG. 23 is a graph of $\beta'_{Ce}$ versus $\beta_{SP}$ for all classifications including intimal fibroplasia samples.

FIG. 23 shows a plot of $\beta'_{Ce}$ vs $\beta_{SP}$ which includes the intimal fibroplasia samples. The divisions in this plot indicate a different decision surface for classification of tissue type than that in FIG. 22. This surface correctly diagnoses 88% of the samples. In this case, the sensitivity of the scheme is 91%, while its specificity is 85%. This decision surface has a predictive value of 85%. The poorer performance of the binary scheme when intimal fibroplasia is included reflects the fact that intimal fibroplasia is an initial step in the formation of atherosclerosis. Thus, this tissue type is more difficult to differentiate from samples displaying well developed atherosclerotic plaques.

The decision surfaces discussed above were drawn to maximize the percentage of correctly diagnosed samples. However, for certain applications it might be more advantageous to maximize other parameters such as sensitivity, specificity or predictive value. For example, a diagnostic procedure to control laser ablation of atherosclerosis should maximize specificity in order to avoid perforation of the artery wall.

It is important to consider probability distributions for each of the parameters to assist in determining the best diagnostic criteria. For simplicity, these have been analyzed with normal distributions truncated at $\beta=0$[23]. The form of this distribution is given by:

$$\frac{\frac{1}{\sqrt{2\pi}\,\sigma}\exp\left[\frac{-(\beta-m)^2}{2\sigma^2}\right]}{\left[1-\frac{1}{\sqrt{2\pi}}\int_{-\infty}^{-m/\sigma}\exp(-t^2/2)dt\right]} \quad (13)$$

Here, m and $\sigma$ no longer refer to the mean and standard deviation of the truncated distribution. These quantities can be easily evaluated and are found in N. L. Johnson, S. Koty, "Distributions in Statistics, Houghton Miffllen Co., Boston, 1970. In applying this form of distribution to the data, m and $\sigma$ were varied, in an iterative fashion, until the mean and variance of the truncated distribution were within 1% of those for the data. Fibretic/sclerotic samples have been excluded from this discussion because of the small sample number.

Figure 24:
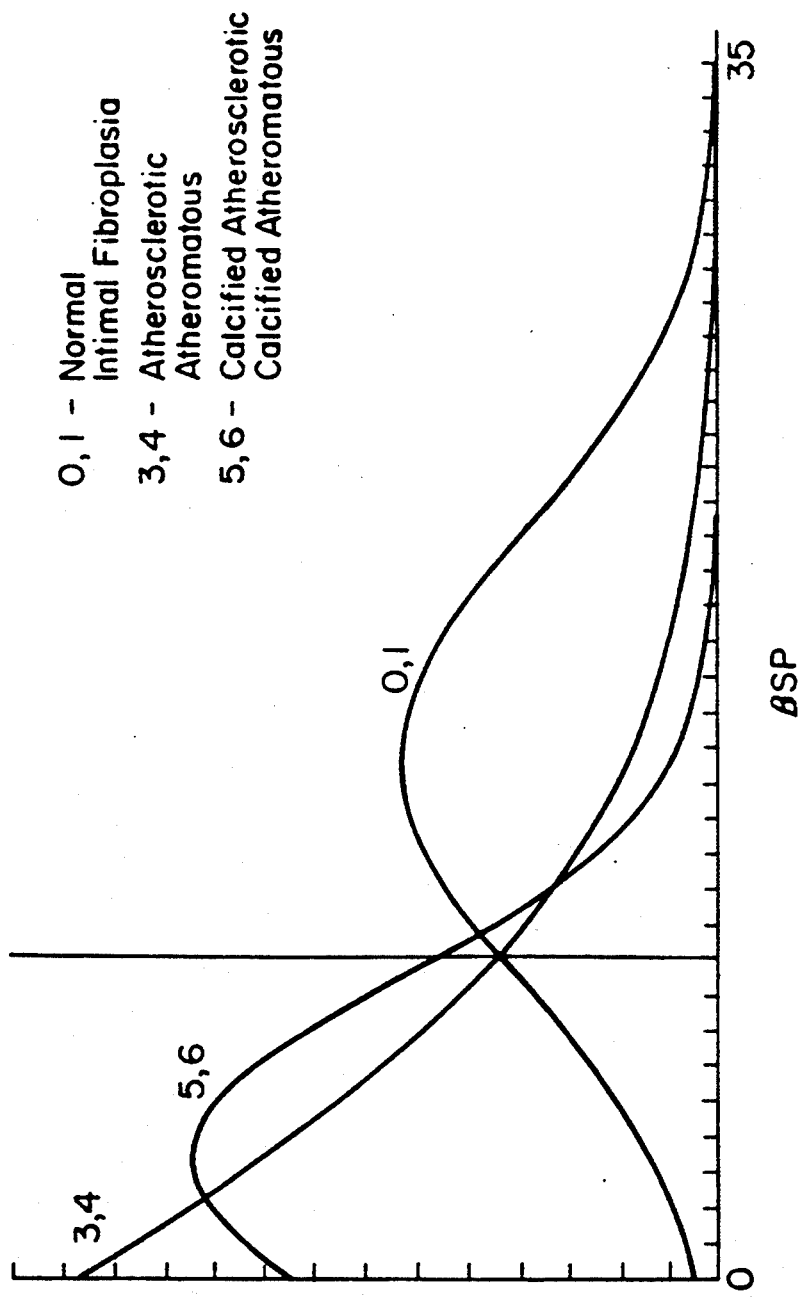
FIG. 24 is a graphical illustration of truncated normal distributions of $\beta$HSPY.

FIG. 24 shows truncated normal distributions for $\beta_{SP}$. These distributions were not greatly different from histograms of the data given in FIG. 18, and can therefore be considered reasonable approximations. Using the same decision vector as in FIG. 18, the sensitivity, specificity and predictive value were assessed using the area under the distribution. These quantities were found to be 79%, 82% and 90%, respectively, close to those values calculated from FIG. 18.

Figure 25:
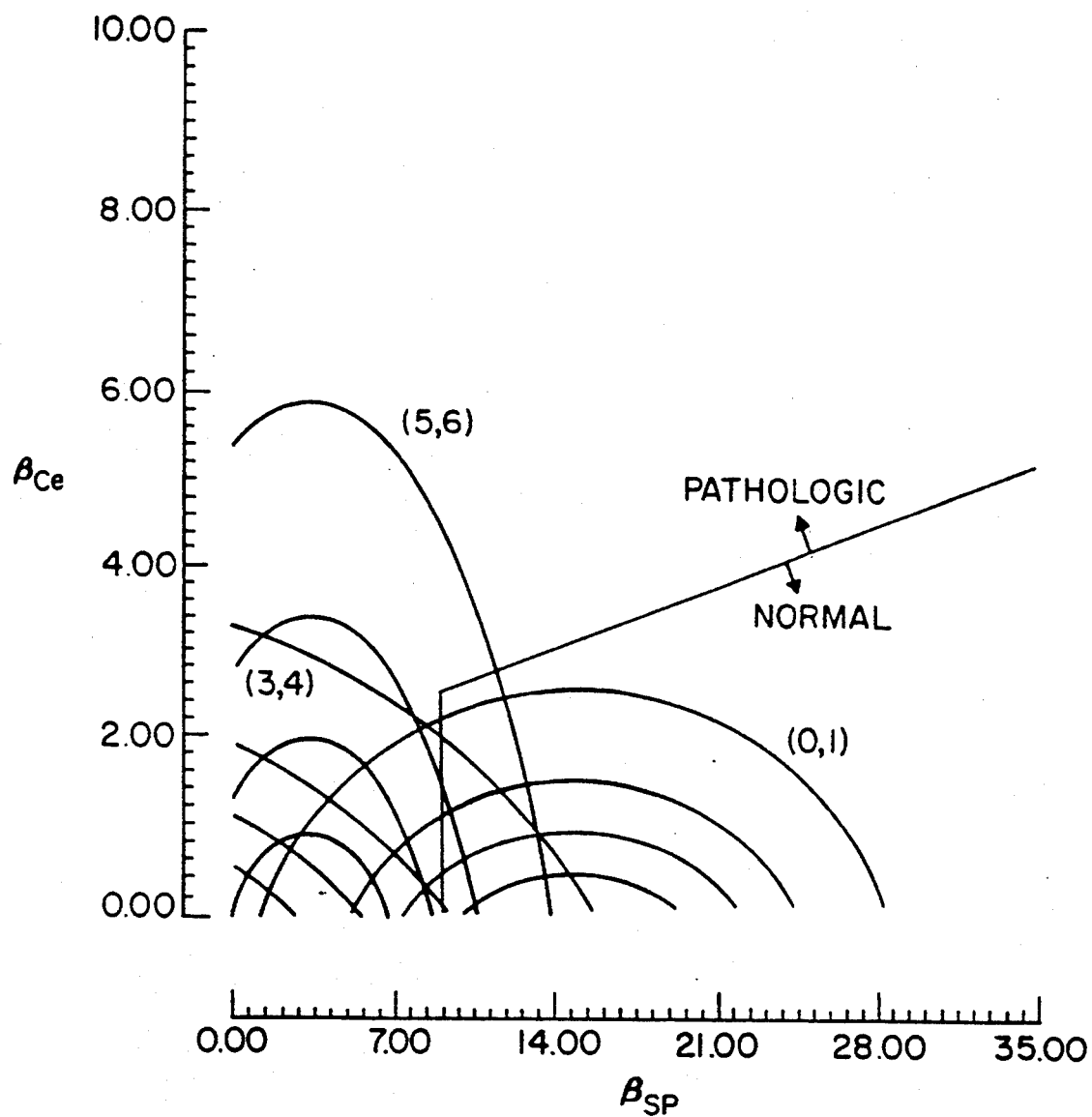
FIG. 25 is a representation of the truncated normal probability distributions of the binary classification scheme of $\beta'_{Ce}$ versus $\beta_{SP}$ shown as a contour plot.

A representation of the truncated normal probability distributions for the binary classification scheme $\beta'_{Ce}$ vs $\beta_{SP}$ is shown in FIG. 25 as a contour plot. The decision surface is that of FIG. 23. Similar to the method used for the single truncated normal distribution for $\beta_{SP}$, the sensitivity, specificity and predictive value were found to be 82%, and 88%.

From FIGS. 24 and 25, the probability that a given value of $\beta'_{Ce}$ and/or $\beta_{SP}$ corresponds to a given type of tissue cannot be determined. This requires a priori knowledge of the relative normal and diseased sample populations. However, FIGS. 24 and 25 provide the values for sensitivity, specificity and predictive value.

The above presents a method for analyzing fluorescence spectra of human tissues with the goal of diagnosing the presence of pathology. The method of tissue fluorescence was developed, and the steps necessary for applying this method to a specific type of tissue were described. It has been established that analysis of tissue fluorescence data within the framework of the method yields two related types of information, the chemical composition of the tissue and the tissue type.

This method was followed for the specific example of 476 nm LIF from human aorta but can be employed with any type of tissue. The fluorescence and attenuation lineshapes necessary for application of the method were determined. Data from 148 samples were analyzed, and it was shown that the method parameters could be correlated to the chemical composition of the tissue, namely the structural protein, ceroid and hemoglobin concentrations. In addition, several diagnostic procedures for the presence of atherosclerosis were defined and evaluated, using the method parameters. Finally, statistical distributions for the parameters with respect to sample type were presented, providing the data necessary to develop specially tailored diagnostic procedures for the presence of atherosclerosis.

The method presented here allows for separation of normal and atherosclerotic tissues. However, the method can be used to separate tissues of each classification (Table 1). Another embodiment of the current method extends to two layers which allow extraction of an additional parameter, the thickness of the first layer, which improves the ability to separate tissue types.

The model can also be extended to include the layered structure of tissue and additional chromophores. In addition, independent measures of tissue fluorescence efficiency and oxy-hemoglobin concentration can be obtained in order to correlate these values to those calculated in the model.

We claim:

1. A method of irradiating chromophores in endogenous tissue to identify tissue composition comprising:
   selecting a known excitation wavelength of the chromophore within a range of wavelengths at which the chromophore undergoes fluorescence;
   irradiating the endogeneous tissue with radiation having at least the selected excitation wavelength within the range;
   detecting a fluorescence emission of the tissue resulting from the irradiation thereof;
   analyzing the detected emission to determine the presence of the chromophore in the tissue;
   forming an attenuation spectrum for a tissue component; and
   modulating the detected emission with the attenuation spectrum.

2. The method of irradiating chromophores of claim 1 wherein the step of forming the attenuation spectrum comprises detecting absorption and scattering components of light incident upon the tissue.

3. The method of irradiating chromophores of claim 1 further comprising the steps of:
   selecting a second known excitation wavelength of a second chromophore at which the second chromophore undergoes fluorescence;
   irradiating simultaneously the endogeneous tissue with radiation having the second wavelength;
   detecting a second fluorescence emission of the tissue resulting from the irradiation within the second wavelength; and
   analyzing the second detected fluorescence emission to determine the presence of the second chromophore in the tissue.

4. The method of claim 3 further comprising illuminating the tissue at additional selected wavelengths to induce fluorescence of additional chromophores and determining additional pathological characteristics of the tissue.

5. The method of irradiating chromophores of claim 3 further comprising the step of determining the wavelength of peak fluorescence of the first and second chromophores within the first and second emissions.

6. The method of irradiating chromophores of claim 5 further comprising the step of determining the ratio of the two fluorescence peaks.

7. The method of irradiating chromophores of claim 1 further comprising the step of determining the wavelength of peak fluorescence of the chromophore within the emission and determining the ratio of the peak with a selected valley within the emission.

8. The method of irradiating chromophores of claim 1 further comprising determining the concentration of the chromophore within the tissue.

9. The method of claim 1 further comprising:
inserting a catheter containing a multiplicity of optical fibers into an artery in the body and positioning a distal end of said catheter adjacent to tissue to be diagnosed; and
coupling a light source to at least one of said fibers to direct light out of a distal end of the optical fiber or fibers to which the light source is coupled.

10. The method of irradiating chromophores of claim 1 wherein the chromophore comprises tryptophan in arterial tissue.

11. The method of irradiating chromophores of claim 1 wherein the chromophore comprises collagen.

12. The method of irradiating chromophores of claim 1 wherein the chromophore comprises elastin.

13. A method of irradiating chromophores in endogenous tissue to identify tissue composition comprising:
selecting a known excitation wavelength of the chromophore within a range of wavelengths at which the chromophore undergoes fluorescence;
irradiating the endogeneous tissue with radiation having at least the selected excitation wavelength within the range;
detecting a fluorescence emission of the tissue resulting from the irradiation thereof;
analyzing the detected emission to determine the presence of the chromophore in the tissue, including separating a component of the emission resulting from reabsorption by the tissue.

14. The method of irradiating chromophores of claim 13 further comprising forming an attenuation spectrum for a tissue component; and modulating the detected emission with the attenuation spectrum.

15. The method of irradiation chromophores of claim 14 wherein the step of forming the attenuation spectrum comprises detecting absorption and scattering components of light incident upon the tissue.

16. The method of irradiating chromophores of claim 13 further comprising the steps of:
selecting a second known excitation wavelength of a second chromophore at which the second chromophore undergoes fluorescence;
irradiating simultaneously the endogeneous tissue with radiation having the second wavelength;
detecting a second fluorescence emission of the tissue resulting from the irradiation within the second wavelength; and
analyzing the second detected emission to determine the presence of the second chromophore in the tissue.

17. A method of irradiating chromophores in endogenous tissue to identify tissue composition comprising:
selecting a known excitation wavelength of the chromophore within a range of wavelengths at which the chromophore undergoes fluorescence;
inserting a fiber optic probe into the body of a patient;
irradiating the endogeneous tissue with the fiber optic probe using radiation having at least the selected excitation wavelength within the range;
detecting a fluorescence emission of the tissue resulting from the irradiation thereof;
analyzing the detected emission to determine the presence of the chromophore in the tissue; and
determining the concentration of the chromophore within the tissue.

* * * * *

UNITED STATES PATENT AND TRADEMARK OFFICE
CERTIFICATE OF CORRECTION

PATENT NO. : 5,419,323
DATED : May 30, 1995
INVENTOR(S) : Carter Kittrell, et al.

It is certified that error appears in the above-indentified patent and that said Letters Patent is hereby corrected as shown below:

At column 1, after the title on line 5, before the Background of the Invention paragraph, please insert the following paragraph:

---This invention was made with government support under Grant Number NIH-5-P41-RR02594 awarded by the National Institutes of Health. The government has certain rights in the invention.---

Signed and Sealed this

Fifth Day of November, 1996

*Attest:*

BRUCE LEHMAN

*Attesting Officer*     *Commissioner of Patents and Trademarks*